(12) United States Patent
Koizumi et al.

(10) Patent No.: US 11,445,723 B2
(45) Date of Patent: Sep. 20, 2022

(54) METHOD AND CONTAINER FOR PRESERVING CORNEAL ENDOTHELIAL CELLS

(71) Applicant: The Doshisha, Kyoto (JP)

(72) Inventors: Noriko Koizumi, Kyoto (JP); Naoki Okumura, Kyoto (JP)

(73) Assignee: The Doshisha, Kyoto (JP)

( * ) Notice: Subject to any disclaimer, the term of this patent is extended or adjusted under 35 U.S.C. 154(b) by 0 days.

(21) Appl. No.: 16/645,145

(22) PCT Filed: Oct. 2, 2019

(86) PCT No.: PCT/JP2019/038961
§ 371 (c)(1),
(2) Date: Oct. 1, 2020

(87) PCT Pub. No.: WO2020/071438
PCT Pub. Date: Apr. 9, 2020

(65) Prior Publication Data
US 2021/0153499 A1    May 27, 2021

(30) Foreign Application Priority Data

Oct. 2, 2018   (JP) .............................. JP2018-187754
Dec. 28, 2018  (JP) .............................. JP2018-247970

(51) Int. Cl.
*A01N 1/00*   (2006.01)
*C12M 3/00*   (2006.01)
(Continued)

(52) U.S. Cl.
CPC .............. *A01N 1/0263* (2013.01); *A61F 2/14* (2013.01); *C12N 5/0621* (2013.01)

(58) Field of Classification Search
CPC ........ C12N 5/0621; A01N 1/0263; A61F 2/14
See application file for complete search history.

(56) References Cited

U.S. PATENT DOCUMENTS

2008/0294149 A1*  11/2008  Krolman ................. A01N 1/02
                                                                         606/1
2009/0232772 A1    9/2009  Amano et al.
(Continued)

FOREIGN PATENT DOCUMENTS

JP    2015-155400 A    8/2015
JP    2015-166323 A    9/2015
(Continued)

OTHER PUBLICATIONS

Okamura et al., Inhibition of TGF-? signaling enables human corneal endothelial cell expansion in vitro for use in regenerative medicine, PLoS One, 8(2):e58000 (2013).
(Continued)

*Primary Examiner* — Nathan A Bowers
(74) *Attorney, Agent, or Firm* — Marshall, Gerstein & Borun LLP

(57) ABSTRACT

The present disclosure provides a method of preserving corneal endothelial cells at a high cell survival rate. The present disclosure provides a method of preserving corneal endothelial cells and/or corneal endothelium-like cells, comprising preserving the corneal endothelial cells and corneal endothelium-like cells in a container with a bottom area of at least about 0.7 cm². Accordingly to the present invention, corneal endothelial cells can be preserved at a high cell survival rate. Corneal endothelial cells preserved in this manner have functions of normal corneal endothelial cells. Such cells can also be used as cells for treating a corneal endothelial disease or the like.

15 Claims, 10 Drawing Sheets

A

B

(51) Int. Cl.
*A01N 1/02* (2006.01)
*A61F 2/14* (2006.01)
*C12N 5/079* (2010.01)

(56) References Cited

U.S. PATENT DOCUMENTS

| | | | |
|---|---|---|---|
| 2010/0209402 A1 | 8/2010 | Koizumi et al. | |
| 2011/0287542 A1* | 11/2011 | Wilson | C12N 5/0602 |
| | | | 435/395 |
| 2015/0218503 A1* | 8/2015 | Kiyama | C12M 23/22 |
| | | | 435/297.1 |
| 2016/0008408 A1* | 1/2016 | Imagawa | C12N 5/0602 |
| | | | 435/371 |
| 2016/0029618 A1* | 2/2016 | Gain | A01N 1/0247 |
| | | | 435/284.1 |
| 2016/0168529 A1* | 6/2016 | Taniguchi | A61M 1/3621 |
| | | | 435/383 |
| 2016/0244711 A1* | 8/2016 | Kiyama | C12M 41/34 |
| 2017/0002318 A1 | 1/2017 | Koizumi et al. | |
| 2017/0340677 A1 | 11/2017 | Shimmura et al. | |
| 2019/0297876 A1* | 10/2019 | Bettini | A01N 1/0242 |

FOREIGN PATENT DOCUMENTS

| | | |
|---|---|---|
| JP | 2016-539641 A | 12/2016 |
| WO | WO-2005/038015 A1 | 4/2005 |
| WO | WO-2006/092804 A2 | 9/2006 |
| WO | WO-2006/092894 A1 | 9/2006 |
| WO | WO-2009/028631 A1 | 3/2009 |
| WO | WO-2016/093359 A1 | 6/2016 |

OTHER PUBLICATIONS

Hongo et al., The effect of a p38 mitogen-activated protein kinase inhibitor on cellular senescence of cultivated human corneal endothelial cells, Invest. Ophthalmol. Vis. Sci., 58:3325-34 (2017).

International Application No. PCT/JP2019/038961, International Search Report, dated Dec. 10, 2019.

Japanese Patent Application No. 2019-070230, First Office Action, dated May 10, 2019.

Japanese Patent Application No. 2019-070230, Second Office Action, dated Sep. 26, 2019.

Kinoshita et al., Injection of Cultured Cells with a ROCK Inhibitor for Bullous Keratopathy, N. Engl. J. Med., 378(11):995-1003 (Mar. 2018).

Nakahara et al., Corneal endothelial expansion promoted by human bone marrow mesenchymal stem cell-derived conditioned medium, PLoS One, 8(7):e69009 (Jul. 2013).

Nipro, Nipro VA syringe, Package Insert, prepared Dec. 2013, revised May 2017.

Nipro, Nipro Syringe, Package Insert, Revised May 2017 (Third Edition).

Nipro, Syringe Package Insert, Information for Medical Practitioners, Syringe, downloaded from the Internet at: <http://med.nipro.co.jp/med_eq_category_detail?id=a1U1000000b531HEAq&name=%E3%83%AA%E3%83%B3%E3%82%B8#FeatureHeadline> (Nov. 11, 2019).

Okamura et al., Inhibition of TGF-beta signaling enables human corneal endothelial cell expansion in vitro for use in regenerative medicine, PLoS One, 8(2):e58000 (2013).

Okumura et al., Enhancement on primate corneal endothelial cell survival in vitro by a ROCK inhibitor, Invest. Ophthalmol. Vis. Sci., 50(8):3680-7 (Aug. 2009).

Summary of Protocols and Hints for Biological Experiment, Mar. 9, 2018.

Zhang et al., Construction of tissue-engineered full-thickness cornea substitute using limbal epithelial cell-like and corneal endothelial cell-like cells derived from human embryonic stem cells, Biomaterials, 124:180-94 (Apr. 2017).

European Patent Application No. 19868572.9, Extended European Search Report, dated May 27, 2022.

Chinese Patent Application No. 201980064646.7, Office Action, dated Jun. 15, 2022.

* cited by examiner

Results of counting before/after preservation (%)

Syringe + amount of air
Results of counting before/after preservation (%)

[Fig. 10]

METHOD AND CONTAINER FOR PRESERVING CORNEAL ENDOTHELIAL CELLS

TECHNICAL FIELD

The present disclosure relates to a technology for preserving corneal endothelial cells.

BACKGROUND ART

Visual information is recognized when light transmitted into the cornea, which is a transparent tissue at the frontmost part of an eye ball, reaches the retina and excites nerve cells of the retina, and a generated electric signal is transmitted through the optic nerve to the visual cortex of the cerebrum. To attain good vision, it is necessary that the cornea is transparent. The transparency of the cornea is maintained by maintaining constant water content by the pump and barrier functions of corneal endothelial cells.

While human corneal endothelial cells are present at a density of about 3000 cell per 1 $mm^2$ at birth, once severely damaged, corneal endothelial cells cannot maintain their function such that transparency of the cornea is lost due to the limited ability of the cells to regenerate. Corneal endothelial dystrophy or bullous keratopathy induced by corneal endothelial dysfunction due to various causes results in edema or turbidity of the cornea, leading to significant deterioration in vision. Currently, heterologous corneal transplant using a donor cornea is performed for bullous keratopathy. However, many problems remain to be solved for corneal transplantation, such as invasiveness of surgery, rejection, and shortage in donors.

To overcome such problems, cell transplant therapy with low invasiveness have been developed in recent years as therapy for corneal endothelial diseases (Non Patent Literature 1). Culture of corneal endothelial cells is challenging, and involves problems such as inability to grow with conventional methods (Non Patent Literatures 2 and 3), fibroblast formation (Non Patent Literature 4), and cellular senescence (Non Patent Literature 5). Culturing methods of corneal endothelial cells are being actively studied, and in fact have become clinically applicable (Non Patent Literature 1).

CITATION LIST

Non Patent Literature

[NPL 1] Kinoshita S, Koizumi N, Ueno M, et al. Injection of cultured cells with a ROCK inhibitor for bullous keratopathy. N Engl J Med 2018; 378: 995-1003.
[NPL 2] Okumura N, Ueno M, Koizumi N, et al. Enhancement on primate corneal endothelial cell survival in vitro by a ROCK inhibitor. Invest Ophthalmol Vis Sci 2009; 50:3680-3687.
[NPL 3] Nakahara M, Okumura N, Kay E P, et al. Corneal endothelial expansion promoted by human bone marrow mesenchymal stem cell-derived conditioned medium. PLoS One 2013; 8:e69009.
[NPL 4] Okumura N, Kay E P, Nakahara M, Hamuro J, Kinoshita S, Koizumi N. Inhibition of TGF-beta Signaling Enables Human Corneal Endothelial Cell Expansion In Vitro for Use in Regenerative Medicine. PLoS One 2013; 8:e58000.
[NPL 5] Hongo A, Okumura N, Nakahara M, Kay E P, Koizumi N. The Effect of a p38 Mitogen-Activated Protein Kinase Inhibitor on Cellular Senescence of Cultivated Human Corneal Endothelial Cells. Invest Ophthalmol Vis Sci 2017; 58: 3325-3334.

SUMMARY OF INVENTION

Solution to Problem

The inventors have come to discover a method of preserving corneal endothelial cells at a high survival rate as a result of diligent study. Specifically, the inventors found that corneal endothelial cells are maintained at a high survival rate by preserving the cells in a container with a specific bottom area. Corneal endothelial cells preserved in this manner have functions of normal corneal endothelial cells. Thus, the present disclosure provide corneal endothelial cells that are ready-to-use substantially without additional manipulation as therapeutic cells.

Therefore, the present disclosure provides the following.
(Item 1)
A method of preserving corneal endothelial cells and/or corneal endothelium-like cells, comprising preserving the corneal endothelial cells and/or corneal endothelium-like cells in a container with a bottom area of at least about 0.7 $cm^2$.
(Item 2)
The method of item 1, wherein a liquid surface of a liquid for preserving the cells is about 0.75 mm or greater.
(Item 3)
The method of item 1 or 2, wherein the bottom area of the container is about 0.7 to about 4 $cm^2$.
(Item 4)
The method of any one of items 1 to 3, wherein the bottom area of the container is about 1.5 to about 3 $cm^2$.
(Item 5)
The method of any one of items 1 to 4, wherein the bottom area of the container is about 1.8 to about 2 $cm^2$.
(Item 6)
The method of any one of items 1 to 5, wherein the container has not been surface treated for adherent culture.
(Item 7)
The method of any one of items 1 to 6, wherein the container is a container with a low adhesion surface or a container with an untreated surface.
(Item 8)
The method of any one of items 1 to 7, wherein the container is made of polystyrene, polypropylene, or glass.
(Item 9)
The method of any one of items 1 to 8, wherein the container is selected from the group consisting of a 24-well plate, a vial bottle, a syringe, and a dish.
(Item 10)
The method of any one of items 1 to 9, wherein the cells are preserved at a temperature of about 12° C. to about 42° C.
(Item 11)
The method of any one of items 1 to 10, wherein the cells are preserved at a temperature of about 17° C. to about 39° C.
(Item 12)
The method of any one of items 1 to 11, wherein the cells are preserved at a temperature of about 27° C. to about 37° C.
(Item 13)
The method of any one of items 1 to 12, wherein the cells are preserved at a temperature of about 37° C.

(Item 14)
A container for preserving corneal endothelial cells and/or corneal endothelium-like cells, wherein a bottom area is at least about 0.7 cm$^2$.
(Item 15)
The container of item 14, wherein the container has a structure that permits a height of a liquid surface to be about 0.75 mm or greater.
(Item 16)
The container for preserving corneal endothelial cells and/or corneal endothelium-like cells of item 14 or 15, wherein a bottom area is about 0.7 to about 4 cm$^2$.
(Item 17)
The container of any one of items 14 to 16, wherein the bottom area of the container is about 1.5 to about 3 cm$^2$.
(Item 18)
The container of any one of items 14 to 17, wherein the bottom area of the container is about 1.8 to about 2 cm$^2$.
(Item 19)
The container of any one of items 14 to 18, wherein the container has not been surface treated for adherent culture.
(Item 20)
The container of any one of items 14 to 19, wherein the container is a container with a low adhesion surface or a container with an untreated surface.
(Item 21)
The container of any one of items 14 to 20, wherein the container is made of polystyrene, polypropylene, or glass.
(Item 22)
The container of any one of items 14 to 21, wherein the container is selected from the group consisting of a 24-well plate, a vial bottle, a syringe, and a dish.
(Item 23)
Corneal endothelial cells or corneal endothelium-like cells preserved by the method of any one of items 1 to 13.
(Item 24)
A composition for treating or preventing a corneal endothelial disorder, disease, or symptom, comprising the corneal endothelial cells and/or corneal endothelium-like cells of item 23.
(Item 25)
The composition of item 24, further comprising a ROCK inhibitor.
(Item 26)
The composition of item 25, wherein the composition is characterized by being administered in conjunction with a ROCK inhibitor.
(Item 27)
The composition of item 25 or 26, wherein the ROCK inhibitor is Y-27632.
(Item 28)
A cell-containing container comprising (A) corneal endothelial cells and/or corneal endothelium-like cells and (B) a container for preserving the corneal endothelial cells and/or corneal endothelium-like cells, wherein a bottom area is at least about 0.7 cm$^2$.
(Item 29)
The cell-containing container of item 28, further comprising a feature of one or more of items 15 to 22.
(Item 30)
The cell-containing container of item 28 or 29, further comprising a ROCK inhibitor.

The present invention also provides the following items.
(Item 1A)
A method of preserving corneal endothelial cells and/or corneal endothelium-like cells, comprising preserving the corneal endothelial cells and/or corneal endothelium-like cells in a container with a bottom area of at least about 0.7 cm$^2$.
(Item 2A)
The method of item 1A, wherein the corneal endothelial cells and corneal endothelium-like cells are clinically applicable cells.
(Item 3A)
The method of item 1A or 2A, wherein the preserved corneal endothelial cells and corneal endothelium-like cells are characterized by being administered without additional processing or culturing.
(Item 4A)
The method of any one of items 1A to 3A, wherein the preservation is made for at least about 6 hours.
(Item 5A)
The method of any one of items 1A to 4A, wherein a height of a liquid surface of a liquid for preserving the cells is about 0.75 mm or greater.
(Item 6A)
The method of any one of items 1A to 5A, wherein the bottom area of the container is about 0.7 to about 4 cm$^2$.
(Item 7A)
The method of any one of items 1A to 6A, wherein the bottom area of the container is about 1.5 to about 3 cm$^2$.
(Item 8A)
The method of any one of items 1A to 7A, wherein the bottom area of the container is about 1.8 to about 2 cm$^2$.
(Item 9A)
The method of any one of items 1A to 8A, wherein the container has not been surface treated for adherent culture.
(Item 10A)
The method of any one of items 1A to 9A, wherein the container is a container with a low adhesion surface or a container with an untreated surface.
(Item 11A)
The method of any one of items 1A to 10A, wherein the container is made of polystyrene, polypropylene, or glass.
(Item 12A)
The method of any one of items 1A to 11A, wherein the container is selected from the group consisting of a 24-well plate, a vial bottle, a syringe, and a dish.
(Item 13A)
The method of any one of items 1A to 12A, wherein the cells are preserved at a temperature of about 0° C. to about 42° C.
(Item 14A)
The method of any one of items 1A to 13A, wherein the cells are preserved at a temperature of about 17° C. to about 39° C.
(Item 15A)
The method of any one of items 1A to 14A, wherein the cells are preserved at a temperature of about 27° C. to about 37° C.
(Item 16A)
The method of any one of items 1A to 15A, wherein the cells are preserved at a temperature of about 37° C.
(Item 17A)
The method of any one of items 1A to 16A, wherein the corneal endothelial cells and/or corneal endothelium-like cells are preserved in a state of a cell suspension.
(Item 18A)
The method of any one of items 1A to 17A, wherein a volume of the suspension is at least about 50 μL.
(Item 19A)
The method of any one of items 1A to 18A, wherein a volume of the suspension is about 100 μL to about 2000 μL.

(Item 20A)

The method of any one of items 1A to 19A, wherein the preserved corneal endothelial cells and/or corneal endothelium-like cells can be used in cell injection therapy.

(Item 21A)

The method of any one of items 1A to 20A, wherein a cell density of the cells preserved in the container is about $2\times10^4$ cells/ml to about $8\times10^7$ cells/ml.

(Item 22A)

The method of any one of items 1A to 21A, wherein a cell density of the cells preserved in the container is about $2\times10^6$ cells/ml to about $4\times10^6$ cells/ml.

(Item 23A)

A container for preserving corneal endothelial cells and/or corneal endothelium-like cells, wherein a bottom area is at least about 0.7 cm².

(Item 24A)

The container of item 23A, wherein the container has a structure that permits a height of a liquid surface to be about 0.75 mm or greater.

(Item 25A)

The container for preserving corneal endothelial cells and/or corneal endothelium-like cells of item 23A or 24A, wherein a bottom area is about 0.7 to about 4 cm².

(Item 26A)

The container of any one of items 23A to 25A, wherein the bottom area of the container is about 1.5 to about 3 cm².

(Item 27A)

The container of any one of items 23A to 26A, wherein the bottom area of the container is about 1.8 to about 2 cm².

(Item 28A)

The container of any one of items 23A to 27A, wherein the container has not been surface treated for adherent culture.

(Item 29A)

The container of any one of items 23A to 28A, wherein the container is a container with a low adhesion surface or a container with an untreated surface.

(Item 30A)

The container of any one of items 23A to 29A, wherein the container is made of polystyrene, polypropylene, or glass.

(Item 31A)

The container of any one of items 23A to 30A, wherein the container is selected from the group consisting of a 24-well plate, a vial bottle, a syringe, and a dish.

(Item 32A)

The container of any one of items 23A to 31A, wherein the container is for preserving the corneal endothelial cells and/or corneal endothelium-like cells in a state of a cell suspension.

(Item 33A)

The container of item 32A, wherein the corneal endothelial cells and/or corneal endothelium-like cells can be used in cell injection therapy.

(Item 34A)

The container of any one of items 23A to 33A, wherein the corneal endothelial cells and/or corneal endothelium-like cells are preserved for at least about 6 hours.

(Item 35A)

Corneal endothelial cells or corneal endothelium-like cells preserved by the method of any one of items 1A to 22A.

(Item 36A)

The corneal endothelial cells and/or corneal endothelium-like cells of item 35A, wherein the corneal endothelial cells and/or corneal endothelium-like cells are preserved for at least about 6 hours.

(Item 37A)

A composition for treating or preventing a corneal endothelial disorder, disease, or symptom, comprising the corneal endothelial cells and/or corneal endothelium-like cells of item 35A or 36A.

(Item 38A)

The composition of item 37A, further comprising a ROCK inhibitor.

(Item 39A)

The composition of item 38A, wherein the composition is characterized by being administered in conjunction with a ROCK inhibitor.

(Item 40A)

The composition of item 38A or 39A, wherein the ROCK inhibitor is selected from Y-27632, ripasudil, fasudil, or a pharmaceutically acceptable salt thereof.

(Item 41A)

A cell-containing container comprising (A) corneal endothelial cells and/or corneal endothelium-like cells and (B) a container for preserving the corneal endothelial cells and/or corneal endothelium-like cells, wherein a bottom area is at least about 0.7 cm².

(Item 42A)

The cell-containing container of item 41A, further comprising a feature of one or more of items 24A to 34A.

(Item 43A)

The cell-containing container of item 41A or 42A, further comprising a ROCK inhibitor.

(Item 44A)

The cell-containing container of any one of items 41A to 43A, wherein a cell density of the cells is about $2\times10^4$ cells/ml to about $8\times10^7$ cells/ml.

(Item 45A)

The cell-containing container of any one of items 41A to 44A, wherein a cell count of the cells is about $2\times10^6$ cells/ml to about $4\times10^6$ cells/ml.

(Item 46A)

The cell-containing container of any one of items 41A to 45A, wherein a volume of a suspension of the corneal endothelial cells and/or corneal endothelium-like cells is at least about 50 μL.

(Item 47A)

The method of item 46A, wherein the volume of the suspension is about 300 μl to about 600 μl.

(Item 48A)

A cell formulation comprising corneal endothelial cells and/or corneal endothelium-like cells and a container for preserving the corneal endothelial cells and/or corneal endothelium-like cells, wherein a bottom area of the container is at least about 0.7 cm².

(Item 49A)

The cell formulation of item 48A, wherein the container has a feature of one or more of items 24A to 34A.

(Item 50A)

The cell formulation of item 48A or 49A, wherein the corneal endothelial cells and/or corneal endothelium-like cells are preserved for at least about 6 hours.

(Item 51A)

The cell formulation of any one of items 48A to 50A, wherein the corneal endothelial cells and/or corneal endothelium-like cells are preserved in a suspended state.

(Item 52A)

The cell formulation of any one of items 48A to 51A, wherein the corneal endothelial cells and/or corneal endothelium-like cells preserved in a suspended state can be used in cell injection therapy.

(Item 53A)
A method of treating or preventing a corneal endothelial disorder, disease, or symptom in a subject, comprising administering to the subject an effective amount of corneal endothelial cells and/or corneal endothelium-like cells preserved by the method of any one of items 1A to 22A.
(Item 54A)
The method of item 53A, wherein the corneal endothelial cells and/or corneal endothelium-like cells are preserved for at least about 6 hours.
(Item 55A)
The method of item 53A, wherein the corneal endothelial cells and/or corneal endothelium-like cells are preserved in a state of a cell suspension.
(Item 56A)
The method of item 55A, wherein about 20 μL to about 500 μL of the cell suspension is administered.
(Item 57A)
The method of item 55A, wherein about 200 μL to about 300 μL of the cell suspension is administered.
(Item 58A)
The method of any one of items 53A to 57A, wherein the corneal endothelial cells or corneal endothelium-like cells are administered in conjunction with an effective amount of a ROCK inhibitor.
(Item 59A)
The method of item 58A, wherein the ROCK inhibitor is selected from Y-27632, ripasudil, fasudil, or a pharmaceutically acceptable salt thereof.
(Item 60A)
The method of any one of items 53A to 59A, wherein about 40 thousand to about 4 million cells are administered.
(Item 61A)
The method of any one of items 53A to 60A, wherein about 400 thousand to about 1 million cells are administered.
(Item 62A)
Corneal endothelial cells or corneal endothelium-like cells preserved by the method of any one of items 1A to 22A for treating or preventing a corneal endothelial disorder, disease, or symptom in a subject.
(Item 63A)
Use of corneal endothelial cells or corneal endothelium-like cells preserved by the method of any one of items 1A to 22A in the manufacture of a drug for treating or preventing a corneal endothelial disorder, disease, or symptom in a subject.

The present invention is intended so that one or more of the aforementioned features can be provided not only as the explicitly disclosed combinations, but also as other combinations thereof. Additional embodiments and advantages of the present invention are recognized by those skilled in the art by reading and understanding the following detailed description as needed.

Advantageous Effects of Invention

According to the present invention, corneal endothelial cells can be preserved at a high cell survival rate. Corneal endothelial cells preserved in this manner have functions of normal corneal endothelial cells. Such cells can also be used as cells for treating a corneal endothelial disease or the like. The present disclosure also provides a cell formulation that can be provided in a ready-to-use manner.

BRIEF DESCRIPTION OF DRAWINGS

FIG. 3A shows images, from the left, from day 1, day 7, and day 14 after injection, and images, from the top, of the control eye (no cell injection), eye injected with cells preserved for 24 hours, eye injected with cells preserved for 48 hours, and eye injected with cells preserved for 72 hours.

DESCRIPTION OF EMBODIMENTS

Figure 1:
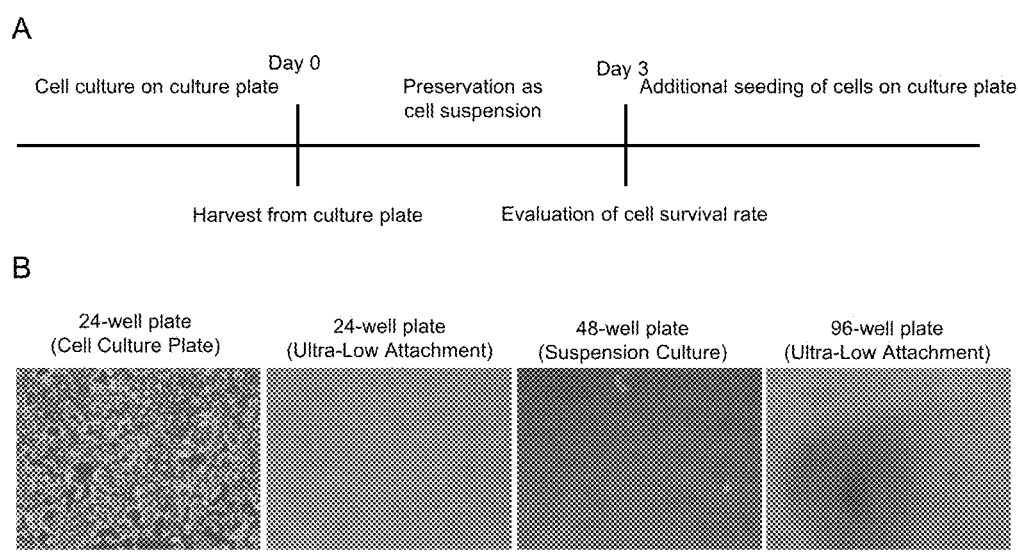
FIG. 1A shows a schematic diagram of an exemplary procedure for preserving corneal endothelial cells.
FIG. 1B shows phase contrast microscope images of each plate, wherein corneal endothelial cells were preserved in a 24-well plate (cell culture plate), 24-well plate (Ultra-Low Attachment), 48-well plate (Suspension Culture), and 96-well plate (Ultra-Low Attachment) and then the cells were collected by gentle pipetting.

The present invention is described hereinafter. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Therefore, unless defined otherwise, all terminologies and scientific technical terms that are used herein have the same meaning as the general understanding of those skilled in the art to which the present invention pertains. In case of a contradiction, the present specification (including the definitions) takes precedence. As used herein, "about" refers to a range of ±10% of the subsequent value.

(Definition)

As used herein, "corneal endothelial cell" is used in the meaning that is commonly used in the art. A cornea is one of the lamellar tissues constituting an eye. A cornea is transparent and positioned at a part closest to the external environment. In humans, it is understood that the cornea is comprised of five layers, i.e., in order from the outside (body surface), corneal epithelium, Bowman's membrane, Lamina propria, Descemet's membrane (corneal endothelial basement membrane), and corneal endothelium. Unless specifically noted otherwise, parts other than the epithelium and endothelium may be collectively referred to as "corneal stroma". The term is also used herein. As used herein, "HCEC" is an abbreviation of human corneal endothelial cells.

As used herein, "corneal endothelium-like cell" refers to a cell differentiated from a stem cell, such as a cell differentiated from an IPS cell, which has substantially the same function as corneal endothelial cells. A method of differentiating stem cells such as ES cells or IPS cells into corneal endothelium-like cells is well known in the art (McCabe et al., PLoS One. 2015 Dec. 21; 10(12): e0145266; Ali et al., Invest Ophthalmol Vis Sci. 2018 May 1; 59 (6): 2437-2444). Briefly, in a typical example, iPS cells are seeded on a 35 mm Matrigel coated plate (Corning) at a 1:12 dilution on day 0 by using a cell dissociation buffer (Life Technologies) (80% confluent plates are separated into 12 plates). The iPS cells are grown in the medium (mTeSR1; STEMCELL Technologies Inc.) for 4 days. On day 4, the mTeSR1 medium is replaced with a Smad inhibitor medium comprising 500 ng/mL human recombinant Noggin (R&D Systems, Minneapolis, Minn., USA) and 10 μM SB431542 (MilliporeSigma) in a basal medium of 80% DMEM-F12 (Life Technologies), 20% KSR (Life Technologies), 1% nonessential amino acid (Life Technologies), 1 mM L-glutamine (STEMCELL Technologies, inc.), 0.1 mM β-mercaptoethanol (MilliporeSigma), and 8 ng/mL βFGF (MilliporeSigma). On day 6, the Smad inhibitor medium is replaced with a cornea medium comprising 0.1×B27 supplement (Life Technologies), 10 ng/mL recombinant human platelet derived growth factor-BB (PDGF-BB; PeproTech, Rocky Hill, N.J., USA), and 10 ng/mL recombinant human Dickkopf related protein-2 (DKK-2; R&D Systems) in a basal medium of 80% DMEM-F12 (Life Technologies), 20% KSR (Life Technologies), 1% nonessential amino acid (Life Technologies), 1 mM L-glutamine (STEMCELL Technologies, inc.), 0.1 mM β-mercaptoethanol (MilliporeSigma), and 8 ng/mL βFGF (MilliporeSigma). On day 7, differentiating CECs are transferred to a new Matrigel coated plate (35 mm) and grown in a cornea medium for another 13 days. Differentiated CECs are collected on day 20. The aforementioned example is merely a typical example. Those skilled in the art can also use other methods that are well known in the art (Fukuta et al., PLoS One. 2014 Dec. 2; 9(12): e112291; Hayashi et al., Nature. 2016 Mar. 17; 531 (7594): 376-80). Those skilled in the art can also make corneal endothelium-like cells by appropriately adjusting the conditions for a method that is well known in the art.

"Corneal endothelial cells" and "corneal endothelium-like cells" can comprise a magnetic component (e.g., iron). For example, injection of corneal endothelial cells comprising a magnetic substance into the anterior chamber can promote adhesion by magnetic attraction toward the inside (e.g., Descemet's membrane) of a corneal with magnetic force (Patel et al., Invest Ophthalmol Vis Sci. 2009 May; 50(5): 2123-31; Mimura et al., Exp Eye Res. 2003 June; 76(6): 745-51; and Mimura et al., Exp Eye Res. 2005 February; 80(2): 149-57). "Magnetic component" refers to a substance that is magnetized by a magnetic field. Examples thereof include iron, cobalt, nickel, ferrite, and the like.

As used herein, "adherent culture" refers to culture that allows cells to adhere to a container. Examples of containers for adherent culture include containers treated with cell culture (TC: tissue culture).

As used herein, "low adhesion" refers to having hardly any cells adhering to a container upon culture or preservation of the cells. Containers with a low adhesion surface have the surface coated with, for example, hydrogel (e.g., by a covalent bond) and/or silica ($SiO_2$). Other examples include glass containers with an IRAS treated surface. IRAS treated vial bottles are available from Iwata Glass Industrial Co., Ltd (Osaka). Alkaline elution from borosilicate glass is suppressed by IRAS treatment. Any treatment, other than IRAS treatment, that suppresses alkaline elusion can also be used in the present disclosure. For example, a container can be coated with LIPIDURE®-CM5206, LIPIDURE®-CR2001, LIPIDURE®-CR3001, LIPIDURE®-PC, or LIPIDURE®-NH01 that is available from NOF Corporation (https://www.nof.co.jp/business/life/product04.html). Containers with a low adhesion surface are commercially available as containers for suspension culture in some cases. A container for suspension culture is considered a container with a low adhesion surface herein, as long as the surface is treated so that cells do not adhere to the container. Containers that are treated with silicoat, (silicon dioxide coat) silicone, sulfur, or the like can also be used.

As used herein, "surface untreated" refers to lack of treatment of a surface. "Container with an untreated surface" refers to a container that can culture or preserve cells without adhesion of the cells to the container in the same manner as a container with a low adhesion surface. Containers with an untreated surface are commercially available as containers for suspension culture in some cases. A container for suspension culture is considered as a container with an untreated surface, as long as the surface is not treated, and cells can be cultured or preserved without adhesion of the cells to the container.

As used herein, "preservation" of cells means storage for a certain period of time (typically, but not limited to, at least 6 hours) in a container for any purpose (e.g., cell injection therapy, or transport therefor), referring to maintaining cells in a container without growth while maintaining the function of the cells. Preservation differs from "culture", which is intended for growing cells. Preservation does not refer to transferring cells into a container such as a syringe immediately prior to administration, or temporarily retaining cells in a container for preparation at the time of use immediately prior to administration.

As used herein, "cell-containing container" refers to a container containing cells (typically corneal endothelial cells or corneal endothelium-like cells). Such a container typically has a feature disclosure herein.

(Preferred Embodiments)

The preferred embodiments are described hereinafter. It is understood that the embodiments are exemplification of the present invention, so that the scope of the present invention is not limited to such preferred embodiments. It is understood that those skilled in the art can refer to the following preferred embodiments to readily make modifications or changes within the scope of the present invention. Any of these embodiments can be appropriately combined by those skilled in the art.

(Preservation Method)

In one aspect, the present disclosure provides a method of preserving corneal endothelial cells and/or corneal endothelium-like cells, comprising preserving the corneal endothelial cells and/or corneal endothelium-like cells in a container with a specific bottom area, and various technologies required for the preservation method (including, for example, a container and the like).

In one embodiment, the bottom area of a container used in the method of the present disclosure can be at least about 0.7 cm$^2$, and can generally be about 0.7 to about 4 cm$^2$. Although not wishing to be bound by any theory, a high cell survival rate cannot be achieved with a container having a bottom area of less than 0.7 cm$^2$ (e.g., 12-well plate). A container having a bottom area greater than 4 cm$^2$ (e.g., 48-well plate) is not suitable for preservation because the liquid surface would be too low when placing a cell suspension or liquid for preserving cells that can be used in corneal endothelial cell injection therapy (e.g., about 300 µl) in a container. In a certain embodiment, the height of a liquid surface of a liquid for preserving cells is preferably about 0.5 mm or greater, about 0.6 mm or greater, about 0.7 mm or greater, about 0.75 mm or greater, about 0.8 mm or greater, about 0.9 mm or greater, about 1.0 mm or greater, about 1.2 mm or greater, about 1.4 mm or greater, about 1.6 mm or greater, about 1.8 mm or greater, or about 2 mm or greater. In a certain embodiment, the liquid surface of a liquid for preserving cells can be about 1.0 mm or less, about 1.5 mm or less, about 1.8 mm or less, about 2 mm or less, about 3 mm or less, about 4 mm or less, about 5 mm or less, about 6 mm or less, about 7 mm or less, about 8 mm or less, about 9 mm or less, about 10 mm or less, about 15 mm or less, about 20 mm or less, or the like. In some embodiments, the bottom area of a container used in the method of the present disclosure can be about 0.7 to about 3.5 cm$^2$, about 0.7 to about 3 cm$^2$, about 0.7 to about 2.5 cm$^2$, about 0.7 to about 2.0 cm$^2$, about 1 to about 4 cm$^2$, about 1 to about 3.5 cm$^2$, about 1 to about 3 cm$^2$, about 1 to about 2.5 cm$^2$, about 1 to about 2 cm$^2$, about 1.5 to about 3 cm$^2$, about 1.5 to about 4 cm$^2$, about 1.6 to about 2.2 m$^2$, or about 1.8 to about 2 m$^2$.

If the amount of preserved corneal endothelial cell suspension is greater than the amount that can be used in corneal endothelial cell injection therapy, the upper limit of the bottom area of a container is not particularly limited. For example, the upper limit in a range of bottom areas can be about 4.5 cm$^2$, about 5 cm$^2$, about 5.5 cm$^2$, about 6 cm$^2$, about 7 cm$^2$, about 8 cm$^2$, about 9 cm$^2$, about 10 cm$^2$, about 15 cm$^2$, about 20 cm$^2$, about 25 cm$^2$, about 30 cm$^2$, about 40 cm$^2$, about 50 cm$^2$, about 60 cm$^2$, about 70 cm$^2$, about 80 cm$^2$, about 90 cm$^2$, or about 100 cm$^2$. The bottom area of a container is preferably about 1.5 to about 3 cm$^2$, and more preferably about 2 cm$^2$. In a specific embodiment, the bottom area of a container is about 1.88 cm$^2$.

Corneal endothelial cells and corneal endothelium-like cells preserved by the method of the present disclosure can be cells that can be used in clinical applications such as cell injection therapy. The preservation method of the present disclosure can maintain a high survival rate and cellular function. Corneal endothelial cells and corneal endothelium-like cells can be maintained in a cell suspension state (including a state where cells are not adhering to the bottom surface of a container and can be readily dispersed by light pipetting), or the so-called "Ready-to-use" state. For this reason, corneal endothelial cells and corneal endothelium-like cells preserved by the method of the present disclosure can also be administered without additional processing (cell detachment/suspension formation from a preservation container by treatment with an agent, isolation of a specific cell from a cell population by an instrument, or the like) or culturing. Therefore, the present disclosure provides cells and containers that can be used as a cell formulation, which can be administered without additional processing or with only minimum manipulation, and cell formulations stored in a container.

In a specific embodiment, cells preserved by the method of the present disclosure can be administered to a subject without cell culture or incubation for 24 hours or more, 18 hours or more, 12 hours or more, preferably 6 hours or more (or any other unit of time) for the purpose of growth and/or re-differentiation.

Therefore, in this aspect, the present disclosure provides a method of preserving a cell formulation comprising corneal endothelial cells and/or corneal endothelium-like cells, comprising preserving the cell formulation comprising the corneal endothelial cells and/or corneal endothelium-like cells in a container with a specific bottom area, and provides a cell formulation that is preserved or preservable by such a preservation method, and a treatment or prevention method using a preserved cell formulation.

In some embodiments, corneal endothelial cells and/or corneal endothelium-like cells can be preserved for at least about 1 hour, at least about 2 hours, at least about 3 hours, at least about 4 hours, at least about 5 hours, at least about 6 hours, at least about 12 hours, at least about 18 hours, or at least about 24 hours. While not intended to be limiting, the preservation method of the present disclosure is intended for preservation for transport of a cell formulation to a medical institution without a cell processing center (CPC). Thus, the period of preservation can be a period of preserving corneal endothelial cells and/or corneal endothelium-like cells for, for example, at least about 3 hours, at least about 6 hours, or longer depending on the distance of transport, after taking into consideration the time required for transport, waiting period until administration, or the like. In a specific embodiment, cells can be preserved up to about 72 hours, up to about 96 hours, or up to about 120 hours in the preservation method of the invention. Although not wishing to be bound by any theory, a survival rate of about 80% was confirmed after about 72 hours of preservation by the preservation method of the present disclosure, and a survival rate of about 57% was confirmed after about 96 hours of such preservation (data not shown), so that a survival rate of at least about 30% can be expected after preservation of about 120 hours. In some embodiments, corneal endothelial cells and/or corneal endothelium-like cells can be preserved in a state of a cell suspension for the aforementioned period of time. It was surprising that corneal endothelial cells and/or corneal endothelium-like cells could be preserved for a certain period of time (e.g., about 6 hours) in a suspended state instead of an adherent state, as shown in the Examples. Although not wishing to be bound by any theory, if cells are preserved in a suspension state, the preserved cells have less tight junctions compared to cells cultured in adherent culture or cells cultured/preserved while forming an aggregate. Tight junctions can be measured by using ZO-1 or the like as an indicator. In some embodiments, the preservation method of the present disclosure does not include the use of a scaffold (substrate that promotes cell adhesion or formation of an aggregate or the like).

In some embodiments, preservation can involve transporting. The preservation method of the present disclosure can withstand vibration during transport. Transport can be ground transport, air transport, or any other transport.

The density of cells preserved in the method of the present disclosure is generally about $2 \times 10^4$ cells/ml or greater. Although not wishing to be bound by any theory, when used in cell injection applications, a therapeutic effect cannot be expected if the cell density is too low. If the cell density is too high, cell death during preservation may be promoted by an increase in overlapping cells. Typically, the cell density can be appropriately determined within the range of about $2 \times 10^4$ cells/ml to about $8 \times 10^7$ cells/ml, preferably about $2 \times 10^4$ cells/ml to about $8 \times 10^7$ cells/ml, more preferably about $2 \times 10^5$ cells/ml to about $8 \times 10^6$ cells/ml, still more preferably about $1 \times 10^6$ cells/ml to about $8 \times 10^6$ cells/ml, and most preferably about $2 \times 10^6$ cells/ml to about $4 \times 10^6$ cells/ml. Those skilled in the art can appropriately determine a suitable cell density in accordance with the application.

The method of the present disclosure enables preservation of corneal endothelial cells while maintaining high cell count and high cell survival rate from the time of starting preservation. For example, assuming all cells at the time of starting preservation to be 100%, the method of the present disclosure can achieve at least a total cell count after preservation of about 30% or greater and a viable cell ratio (viable cells/viable cells+dead cells) of about 70% or greater, preferably a total cell count after preservation of about 50% or greater and a viable cell ratio of about 80% or greater, and most preferably a total cell count after preservation of 70% or greater and a viable cell ratio of about 90% or greater. In a specific embodiment, the method of the present disclosure has a cell survival rate (ratio of viable cell count compared to total cells at the time of starting preservation) of preferably about 30% or greater, more preferably about 60% or greater, still more preferably about 80% or greater, and most preferably about 90% or greater. In another specific embodiment, a viable cell ratio (viable cells/viable cells+dead cells) is preferably about 70% or greater, more preferably about 80% or greater, and most preferably 90% or greater, in addition to the aforementioned cell survival rate.

A bottom area refers to an area of a surface referred to as the bottom surface of a container. The method of the present disclosure is intended for preservation while laying down a syringe sideways. In such a case, the bottom area of a container is the area of a surface on which gravitational force is exerted among the cylindrical curved surface contacted by a cell suspension. Besides the laid down state of a syringe, the area of a surface on which gravitational force is exerted among the surface contacted by a cell suspension is similarly the bottom area when at least a portion of a bottom surface is curved or inclined. Although not wishing to be bound by any theory, this is because the present disclosure discovered that it is important to consider the effect of placing cells on a curved surface on which gravitational force is exerted, and preservation of cells can be improved by defining a bottom area based thereon.

In the present disclosure, the temperature during preservation can be any range of temperatures, as long as cells do not freeze or denature in the range of temperatures. For example, the temperature can be in the range of about 0° C. to about 50° C. This is because the cell survival rate decreases if the temperature is too high or too low. Those skilled in the art can appropriately determine the optimal temperature for preservation. In some embodiments, the temperature during preservation can be about 0° C., about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., or about 50° C. The preferred temperature range during preservation is preferably about 12° C. to about 42° C., more preferably about 17° C. to about 39° C., and still more preferably about 27° C. to about 37° C. In a preferred embodiment, the temperature during preservation can be room temperature of about 37° C. In the most preferred embodiment, the temperature during preservation can be, but not limited to, about 37° C. Those skilled in the art understand that an increase or decrease in the temperature by about several ° C. during preservation/transport (e.g., ±about 1° C., ±about 2° C., ±about 3° C., ±about 4° C., ±about 5° C., or the like) is tolerable. Preferably, the variation in the temperature is ±about 3° C. with the baseline of 37° C.

Corneal endothelial cells can be cells derived from mammals (human, mouse, rat, hamster, rabbit, cat, dog, cow, horse, sheep, monkey, or the like), but are preferably derived from primates and especially preferably derived from humans.

In some embodiments, a container is not surface treated for adherent culture. In some embodiments, a container is a container with a low adhesion surface or a container with an untreated surface. In some embodiments, a container is made of polystyrene, polypropylene, or glass. In a specific embodiment, examples of a container include, but are not limited to, a 24-well plate, a vial bottle, a syringe, a dish, and the like.

The container provided in the present disclosure is capable of preservation without resulting in cell adhesion, or the container may or may not be made of an oxygen permeable material, as long as the specification as a cell formulation is not affected in case of cell adhesion. Examples of oxygen permeable materials include polyethylene, as well as any material that allows permeation of oxygen. A material that does not allow oxygen permeation can be processed to allow oxygen permeation by a method that is well known in the art.

In the present disclosure, a well-known preservation medium that is used in the art can be used as the preservation medium of corneal endothelial cells or corneal endothelium-like cells. A preservation medium with a newly provided composition can also be used, as long as it is suitable for preservation. Examples of preservation medium that can be used include, but are not limited to, OptiMEM-I® (Thermo Fisher Scientific), MEM, DMEM, M199, corneal endothelial cell preservation medium (preservation medium used herein, Generation and Feasibility Assessment of a New Vehicle for Cell-Based Therapy for Treating Corneal Endothelial Dysfunction. Okumura N, Kakutani K, Inoue R, Matsumoto D, Shimada T, Nakahara M, Kiyanagi Y, Itoh T, Koizumi N. PLoS One. 2016 Jun. 29; 11(6): e0158427. doi: 10.1371/journal.pone.0158427. eCollection 2016.PMID: 27355373), and the like.

In some embodiments, the amount of liquid used upon preservation can be about 100 µl to about 2000 µl, preferably about 100 µl to about 1000 µl, more preferably about 200 µl to about 800 µl, and most preferably about 300 µl to about 600 µl, but the amount can be appropriately changed in accordance with the objective. The product specification can be, for example, ±about 5%, ±about 10%, ±about 15%, ±about 20%, ±about 25%, ±about 50%, or the like from the baseline amount (e.g., 300 µl). The amount of liquid used upon preservation can be, for example, at least about 50 µl, such as about 100 µl, about 200 µl, about 300 µl, about 400 µl, about 500 µl, about 600 µl, about 700 µl, about 800 µl, about 900 µl, about 1 ml, about 2 ml, about 3 ml, about 4 ml, about 5 ml, about 6 ml, about 7 ml, about 8 ml, about 9 ml, or about 10 ml. In some embodiments, if injection into both eyes is intended in cell injection therapy, the amount can be 2-fold, 3-fold, or 4-fold of the dosage as the product specification. Even if injection into both eyes is not intended, the amount can be 2-fold, 3-fold, or 4-fold of the dosage as the product specification, as a precaution for failed administration. The aforementioned numerical values can be appropriately combined as the range of the amount of liquid. In some embodiments, corneal endothelial cells and/or corneal endothelium-like cells can be preserved in a state of a cell suspension. The amount of liquid described above can be the amount of cell suspension.

(Container)

In another aspect, the present disclosure provides a container, having a specific bottom area, for preserving corneal endothelial cells or corneal endothelium-like cells. The feature described above, or particularly any embodiment specifically described in (Preservation method) can be employed as the specific feature of a container. Although not wishing to be bound by any theory, providing a container that is suitably processed for preservation of corneal endothelial cells or corneal endothelium-like cells and having a specific bottom area has enabled the provision of a cell formulation materializing Ready-to-use in the present disclosure.

(Cell-Containing Container)

In another aspect, the present disclosure provides a cell-containing container comprising corneal endothelial cells or corneal endothelium-like cells and a container for preserving the corneal endothelial cells or corneal endothelium-like cells, wherein the container used has a specific bottom area. The feature described above, or particularly any embodiment specifically described in (Preservation method) can be employed as the specific feature of a container.

In some embodiments, the container of the present disclosure can comprise a Rho kinase (ROCK) inhibitor. The ROCK inhibitor used in this regard can be any embodiment described herein.

(Corneal Endothelial Cells)

In another embodiment, the present disclosure provides corneal endothelial cells or corneal endothelium-like cells preserved by the method described above. In some embodiments, the corneal endothelial cells or corneal endothelium-like cells of the present disclosure can be for treating or preventing a corneal endothelial disorder, disease, or symptom in a subject.

In another embodiment, the present disclosure provides a composition for treating or preventing a corneal endothelial disorder, disease, or symptom, comprising corneal endothelial cells or corneal endothelium-like cells preserved by the method described above.

In some embodiments, a corneal endothelial disorder, disease, or symptom is selected from the group consisting of Fuchs' endothelial corneal dystrophy, post-corneal transplant disorder, corneal endotheliitis, trauma, ophthalmic surgery, post-ophthalmic laser surgery disorder, aging, posterior polymorphous dystrophy (PPD), congenital hereditary endothelial dystrophy (CHED), idiopathic corneal endothelial disorder, and cytomegalovirus corneal endotheliitis.

In some embodiments, the composition of the present disclosure can comprise a Rho kinase (ROCK) inhibitor, or can be administered in conjunction with a ROCK inhibitor. The corneal endothelial cells or corneal endothelium-like cells of the present disclosure can be administered in conjunction with a ROCK inhibitor. Examples of ROCK inhibitors include compounds disclosed in the following documents: U.S. Pat. No. 4,678,783, Japanese Patent No. 3421217, International Publication No. WO 95/28387, International Publication No. WO 99/20620, International Publication No. WO 99/61403, International Publication No. WO 02/076976, International Publication No. WO 02/076977, International Publication No. WO 2002/083175, International Publication No. WO 02/100833, International Publication No. WO 03/059913, International Publication No. WO 03/062227, International Publication No. WO 2004/009555, International Publication No. WO 2004/022541, International Publication No. WO 2004/108724, International Publication No. WO 2005/003101, International Publication No. WO 2005/039564, International Publication No. WO 2005/034866, International Publication No. WO 2005/037197, International Publication No. WO 2005/037198, International Publication No. WO 2005/035501, International Publication No. WO 2005/035503, International Publication No. WO 2005/035506, International Publication No. WO 2005/080394, International Publication No. WO 2005/103050, International Publication No. WO 2006/057270, International Publication No. WO 2007/026664, and the like. Such compounds can be manufactured by the methods described in the respective documents where the compounds are disclosed. The specific examples thereof include 1-(5-isoquinolinesulfonyl) homopiperazine or a salt thereof (e.g., fasudil (1-(5-isoquinolinesulfonyl) homopiperazine)), (+)-trans-4-(1-aminoethyl)-1-(4-pyridylcarbamoyl)cyclohexane((R)-(+)-trans-(4-pyridyl)-4-(1-aminoethyl)-cyclohexanecarboxamide) or a salt thereof (e.g., Y-27632 ((R)-(+)-trans-(4-pyridyl)-4-(1-aminoethyl)-cyclohexanecarboxamide dihydrochloride monohydrate) and the like), and the like. For these compounds, a commercially available product (Wako Pure Chemical Industries, Ltd., Asahi Kasei Pharma Corporation, or the like) can also suitably be used.

In some embodiments, examples of ROCK inhibitors that can be used include Y-27632 ((+)-trans-4-(1-aminoethyl)-1-(4-pyridylcarbamoyl)cyclohexane), ripasudil (4-fluoro-5-{[(2S)-2-methyl-1,4-diazepan-1-yl]sulfonyl}isoquinoline), fasudil (1-(5-isoquinolinesulfonyl)homopiperadine), and pharmaceutically acceptable salts thereof, but are not limited thereto. For example, other ROCK inhibitors can be used such as (but not limited to) the compounds disclosed in U.S. Pat. No. 4,678,783, Japanese Patent No. 3421217, WO 99/20620, WO 99/61403, WO 02/076976, WO 02/076977, WO 02/100833, WO 03/059913, WO 03/062227, WO 2004/009555, WO 2004/022541, WO 2004/108724, WO 2005/003101, WO 2005/039564, WO 2005/034866, WO 2005/037197, WO 2005/037198, WO 2005/035501, WO 2005/035503, WO 2005/035506, WO 2005/080394, WO 2005/103050, WO 2006/057270, or WO 2007/026664.

(Cell Formulation)

In another aspect, the present disclosure provides a cell formulation comprising corneal endothelial cells and/or corneal endothelium-like cells and a container. A cell formulation is provided, wherein the container used in the cell formulation is suitable for preservation of the corneal endothelial cells and/or corneal endothelium-like cells, and a bottom area of the container is at least about 0.7 $cm^2$. The corneal endothelial cells and/or corneal endothelium-like cells in a formulation are maintained without hardly any decrease in viable cells. Therefore, the cell formulation of the present disclosure is a so-called Ready-to-use formulation that can be directly administered. Such a formulation can be used in cell injection therapy. In some embodiments, the cell formulation of the present disclosure can be for treating or preventing a corneal endothelial disorder, disease, or symptom in a subject. Examples of corneal endothelial disorder, disease, or symptom include, but are not limited to, Fuchs' endothelial corneal dystrophy, post-corneal transplant disorder, corneal endotheliitis, trauma, post-ophthalmic surgery disorder, post-ophthalmic laser surgery disorder, aging, posterior polymorphous dystrophy (PPD), congenital hereditary endothelial dystrophy (CHED), idiopathic corneal endothelial disorder, and cytomegalovirus corneal endotheliitis.

(Therapeutic Method)

In another embodiment, the present disclosure provides a method of treating or preventing a corneal endothelial disorder, disease, or symptom in a subject, comprising administering to the subject corneal endothelial cells or corneal endothelium-like cells preserved by the method of the present disclosure.

The number of cells administered can be at least about 40 thousand because the therapeutic effect would be low if the number is too low. If the corneal endothelial disorder, disease, or symptom is partial, the number can be lower than normal such as at least about 40 thousand, at least about 100 thousand, or preferably at least about 200 thousand. In some embodiments, the number of cells administered can be about 40 thousand to about 4 million, preferably about 100 thousand to about 2 million, more preferably about 200 thousand to about 1.4 million, and most preferably about 400 thousand to about 1 million.

The amount of liquid administered can be appropriately determined by considering the suitable viscosity, the capacity that can be administered to the administration site (e.g., inside the anterior chamber), or the like. In some embodiments, about 20 µL to about 500 µL, preferably about 30 µL to about 400 µL, more preferably about 50 µL to about 400 µL, and most preferably about 200 µL to about 300 µL of liquid (cell suspension) can be administered.

(Use)

In another embodiment, the present disclosure provides use of corneal endothelial cells or corneal endothelium-like cells preserved by the method of the present disclosure in the manufacture of a drug for treating or preventing a corneal endothelial disorder, disease, or symptom in a subject.

The present invention has been described while showing preferred embodiments to facilitate understanding. The present invention is described hereinafter based on the Examples. The above descriptions and the following Examples are not provided to limit the present invention, but are for the sole purpose of exemplification. Thus, the scope of the present invention is not limited to the embodiments and Examples that are specifically disclosed herein and is limited only by the scope of claims.

EXAMPLES

The present invention is more specifically described based on the Examples. It is understood that specifically shown reagents as well as those available from Sigma-Aldrich, BASF Japan Ltd., or the like can be used as the various reagents used in the Examples. Human tissues were handled in accordance with the tenets set forth in the Declaration of Helsinki. Human donor corneas were obtained from SightLife™ (Seattle, Wash.). Corneas were retrieved under the tenets of the Uniform Anatomical Gift Act (UAGA) of the particular state after obtaining a written consent for eye donation for research purposes from the next of kin of the deceased donors. The rabbit experiments were performed according to the protocol approved by the Animal Care and Use Committee of the Doshisha University (Approval No. A18003).

Example 1: Screening the Material and Size of Container for Cell Preservation (Materials and Methods)
(Culture of Corneal Endothelial Cells)

Five human donor corneas were obtained from diseased donors who were 40 years old or older. All corneas were preserved in Optisol (Chiron Vision, Irvine, Calif.) at 4° C. for 14 days or less before use. Human corneal endothelial cells (HCECs) were cultured in accordance with the following protocol. Briefly, Descemet's membranes containing corneal endothelia were mechanically peeled off from the donor corneas and digested by incubating with 1 mg/mL collagenase A (Roche Applied Science, Penzberg, Germany) at 37° C. for 12 hours. After washing the HCECs with OptiMEM-I (Life Technologies Corp., Carlsbad, Calif.), the cells were seeded in one well of a 48-well plate coated with laminin E8 fragments (iMatrix-511; Nippi, Incorporated, Tokyo).

The medium was prepared according to the following protocol. Briefly, OptiMEM-I supplemented with 8% fetal bovine serum (FBS), 5 ng/mL epidermal growth factor (EGF; Thermo Fisher Scientific), 20 µg/mL ascorbic acid (Sigma-Aldrich, St. Louis, Mo.), 200 mg/L calcium chloride, 0.08% chondroitin sulfate (Sigma-Aldrich), and 50 µg/mL gentamicin (Thermo Fisher Scientific) were conditioned with NIH-3T3 for 24 hours. The conditioned medium was then collected, filtered through a 0.22 µm filtration unit (EMD Millipore Corporation, Billerica, Mass.), and used as a medium for HCECs.

The HCECs were cultured at 37° C. in a humidified atmosphere containing 5% $CO_2$. The medium was changed three times a week. For passaging the HCECs, cells were trypsinized with TrypLE™ Select Enzyme (10×) (Thermo Fisher Scientific) for five minutes at 37° C. and seeded at a 1:2 ratio. Cultured HCECs at passages 5 through 9 were used for this study.

The HCECs were washed with $Ca^{2+}$- and $Mg^{2+}$-free phosphate buffered saline (PBS) and trypsinized with TrypLE™ Select Enzyme (10×) for 15 minutes at 37° C. Cells were then recovered from the culture plate, washed twice, centrifuged at 280 G for three minutes, and suspended in OptiMEM-I. HCECs were preserved in a form of cell suspension at a cell density of $1.0 \times 10^6$ cells/300 µl in the serum free vehicle (Cell Therapy Vehicle provided by Cell Science & Technology Institute, Inc. (Miyagi)) at 4° C. or 37° C. for 72 hours. The following cell culture plates, test tubes, and vials were used for screening the sizes and the materials for HCEC-preservation: 24-well plate (Ultra-Low Attachment) (Corning Inc. Corning, N.Y.); 24-well plate (Cell Culture) (Corning Inc. Corning); 24-well plate (Untreated) (AGC Techno Glass Co., Ltd., Shizuoka); 48-well plate (Suspension Culture) (Sumitomo Bakelite Co., Ltd.); 96-well plate (Ultra Low Attachment, round bottom) (Corning Inc.); 96-well plate (Ultra Low Attachment, flat bottom) (Corning Inc.); 15 ml Conical Tube (Ultra-Low Attachment) (Sumitomo Bakelite Co., Ltd., Tokyo); 2 ml Cryovial (Corning Inc. Corning); and 10 ml Glass Vial Bottle (Maruemu Corp., Osaka) (Table 1).

After 72 hours of preservation, HCECs were recovered from cell culture plates, test tubes, or vials with gentle pipetting, centrifuged at 280 G for three minutes, and resuspended in Cell Therapy Vehicle at a cell density of $1.0 \times 10^6$ cells/600 µl. The cell survival rate was determined by staining the dead cells with 0.5%-Trypan Blue stain (Nacalai tesque, Kyoto). As a control, HCECs recovered by trypsinization with TrypLE™ Select Enzyme (10×) were centrifuged at 280 G for three minutes, and resuspended in Cell Therapy Vehicle. Then, the cell survival rate was immediately evaluated without preservation in a form of a cell suspension.

(Results)

(Effect of the Preservation Condition in a Form of Cell Suspension on Cell Survival Rate)

Figure 2:
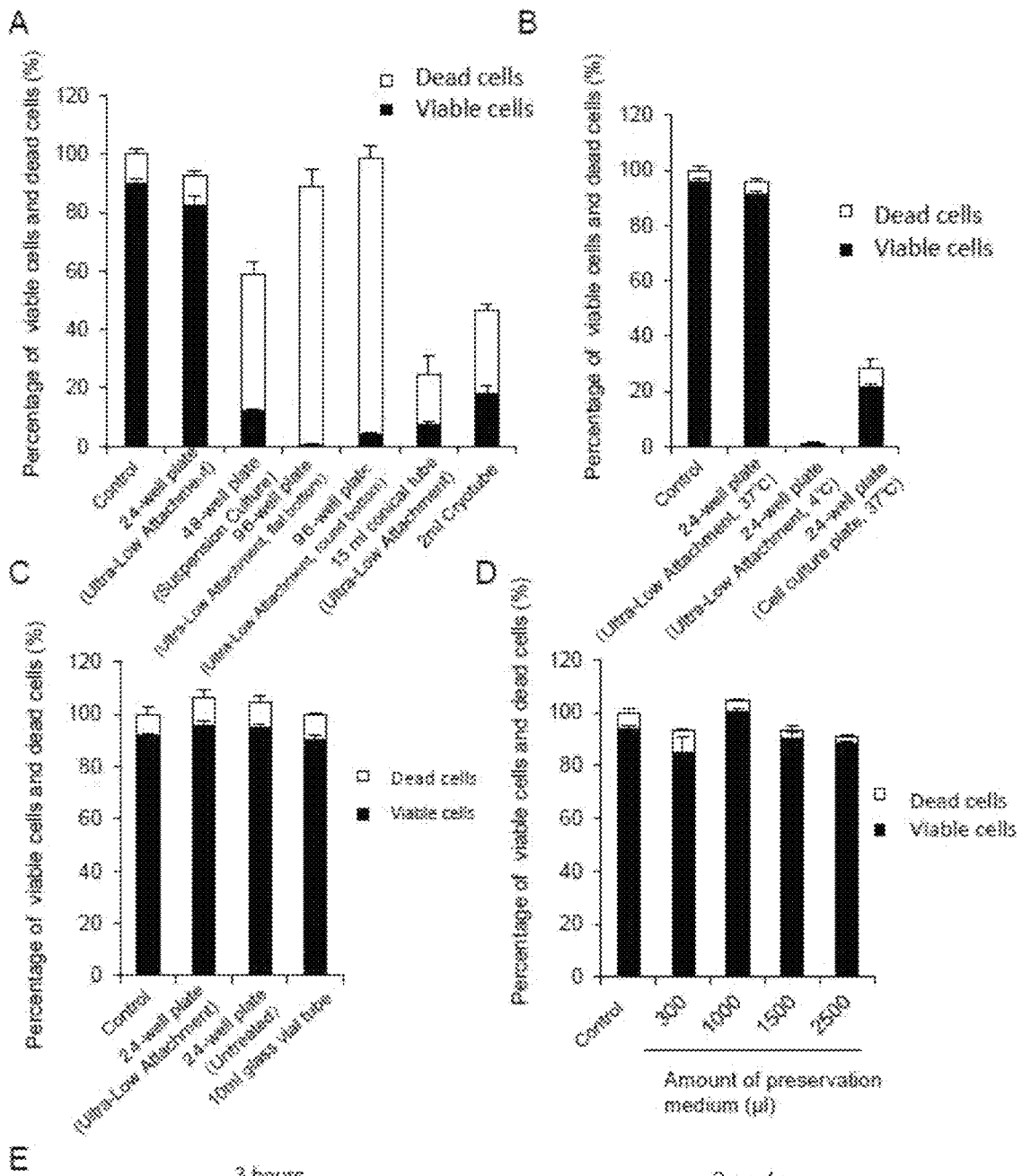
FIG. 2A shows the percentage of viable and dead corneal endothelial cells preserved in a 24-well plate (Ultra-Low Attachment), 48-well plate (Suspension Culture), 96-well plate (Ultra-Low Attachment, flat bottom), 96-well plate (Ultra-Low Attachment, round bottom), 15 ml conical tube (Ultra-Low Attachment), and 2 ml cryotube.
FIG. 2B shows the percentage of viable and dead corneal endothelial cells preserved at 37° C. in a 24-well plate (Ultra-Low Attachment), 4° C. in a 24-well plate (Ultra-Low Attachment),and 37° C. in a 24-well plate (cell culture plate).
FIG. 2C shows the percentage of viable and dead corneal endothelial cells preserved in a 24-well plate (Ultra-Low Attachment), 24-well plate (untreated), and 10 ml glass vial tube.
FIG. 2D shows the percentage of viable and dead corneal endothelial cells preserved in a 24-well plate (Ultra-Low Attachment) in 300 μl, 1000 μl, 1500 μl, and 2500 μl of preservation medium. The white portion of a bar indicates dead cells, and the black portion indicates viable cells.
FIG. 2E shows phase contrast microscope images after 3 hours and after 2 weeks from seeding, on a culture plate, corneal endothelial cells preserved in a 24-well plate (Ultra-Low Attachment).
Figure 2:
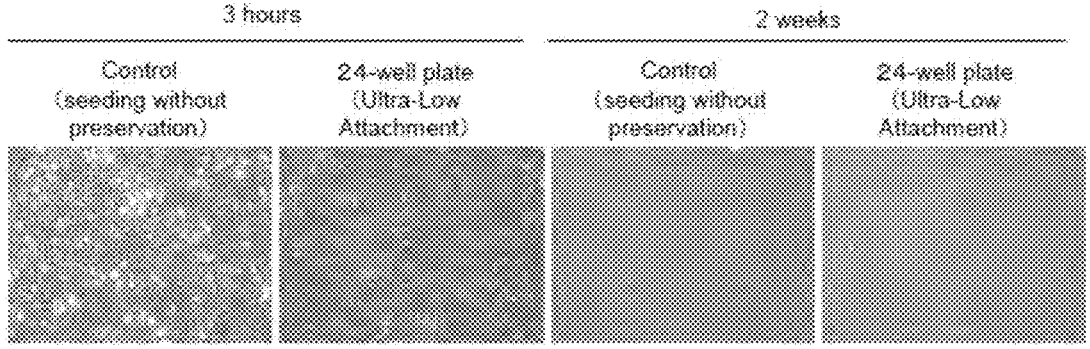

HCECs were preserved at a cell density of $1.0 \times 10^6$ cells/300 µl in a form of a cell suspension in CTV for 72 hours. Cells were retrieved with gentle pipetting, and the cell survival rate was evaluated (FIG. 1A). Phase contrast images showed that 80 to 90% of the area of culture plate for adhesion culture was covered with HCECs after gentle pipetting for cell recovery. On the other hand, almost no cells were observed in any 24-well plate, 48-well plate, and 96 well plate for suspension culture (FIG. 1B). Since surface treatment for adhesion culture was not applicable for HCEC preservation as a form of cell suspension, this Example evaluated the effect of the size and shape of commercially available culture plates and tubes on cell survival rate. Percentage of viable cells and dead cells was 90.3% and 9.7% in the control immediately after being trypsinized and harvested from the culture plate, and the percentages are 82.6% and 10.1% (vs. original number of preserved cells) in cells preserved in the 24 well plate (Ultra-Low Attachment). However, the percentage of viable cells was significantly decreased in comparison to the control in the 48-well plate (Suspension Culture), 96-well plate (Ultra-Low Attachment, flat bottom), 96-well plate (Ultra-Low Attachment, round bottom), 15 ml Conical Tubes (Ultra Low Attachment), and 2 ml Cryovial ($p<0.01$) (FIG. 2A). The number of recovered cells was significantly reduced after preservation in the 48-well plate (Suspension Culture), 15 ml Conical Tubes (Ultra Low Attachment), and 2 ml Cryovial probably due to cell adhesion to the bottom or the wall of the culture plate or test tube. The inventors also evaluated the effect of temperature on the cell survival rate, and showed that almost no cells were recovered after preservation in the 24 well plate (Ultra-Low Attachment) at 4° C. due to massive cell death, though 95.1% of the cells survived at 37° C. (FIG. 2B). Other kinds of culture plate or test tubes without surface treatment for adhesion culture were also evaluated. Consistent with ultra-low attachment in the 24 well plate, an untreated 24 well plate and 10 ml glass vial tube (bottom

TABLE 1

| Preservation | Bottom shape | Diameter (mm) | Bottom area (cm$^2$) | Feature | Material | Manufacturer (model number) |
|---|---|---|---|---|---|---|
| 24-well plate (Ultra-Low Attachment) | Flat | 15 | 1.88 | Ultra-Low Attachment | Polystyrene | Corning (#3473) |
| 15 ml conical tube (Ultra-Low Attachment) | V-shape | 5 | — | Ultra-Low Attachment | Polypropylene | Sumitomo Bakelite (#MS-90150) |
| 2 ml Cryovial | Round | 9 | — | Low Attachment | Polypropylene | Corning (#430488) |
| 10 ml glass vial bottle | Flat | 15 | 2.7 | Untreated | Glass | Maruemu (Vial #No. 3) |
| 24-well plate (Cell Culture) | Flat | 15 | 1.88 | Cell Culture | Polystyrene | Corning (#3526) |
| 24-well plate (Untreated) | Flat | 15 | 1.88 | Untreated | Polystyrene | AGC Techno Glass (#18020-024) |
| 48-well plate (Suspension Culture) | Flat | 9.1 | 0.65 | Suspension Culture | Polystyrene | Sumitomo Bakelite (#MS-8048R) |
| 96-well plate (Ultra-Low Attachment, flat) | Flat | 6.4 | 0.32 | Ultra-Low Attachment | Polystyrene | Corning (#3474) |
| 96-well plate (Ultra-Low Attachment, round) | Round | 6.4 | — | Ultra-Low Attachment | Polystyrene | Corning (#7007) | area was 2.7 cm², similar to the 24 well plate (1.9 cm²)) maintained 90% or greater cell survival rate (FIG. 2C). Medium volume did not significantly alter the survival rate of the cells (FIG. 2D).

HCECKs preserved in a form of a cell suspension in a 24 well plate (Ultra-Low Attachment) were seeded on the culture plate after preservation of 72 hours at 37° C. Representative phase contrast images showed that preserved HCECs adhered on the culture plate without evident cell death after 3 hours of seeding in similar fashion to the control. After 2 weeks, the preserved HCECs formed a monolayer sheet like structure with a polygonal morphology similar to the control (FIG. 2E).

Example 2: Injection of RCECs into Rabbit Corneal Endothelial Decompensation Model (Materials and Methods)
(Rabbit CEC Culture)

Ten rabbit eyes purchased from the Funakoshi Co., Ltd. (Tokyo) were used in this Example. The rabbit CECs (RCECs) were cultured as described above. Briefly, stripped Descemet's membranes with RCECs were incubated with 0.6 U/mL of Accutase (Nacalai Tesque, Kyoto) at 37° C. for 15 minutes, and recovered RCECs were seeded in a culture plate coated with FNC Coating Mix® (Athena Environmental Sciences, Inc., Baltimore, Md.). The RCECs were cultured in Dulbecco's modified Eagle's medium (Life Technologies Corp., Carlsbad, Calif.) supplemented with 10% fetal bovine serum (FBS), 50 U/mL penicillin, 50 µg/mL streptomycin, and 2 ng/mL fibroblast growth factor 2 (Life Technologies Corp.). Cultured RCECs at 1 to 3 passages were used.

(Injection of RCECs into Rabbit Corneal Endothelial Decompensation Model)

The right eye of 12 Japanese white rabbits were used for the experiment. The fellow eye was not used to avoid blindness. The rabbit corneal endothelial decompensation model was made as described above. Briefly, the lens was removed to deepen the anterior chamber one week prior, and the corneal endothelium was mechanically removed with a 20 G silicone needle (Soft Tapered Needle; Inami & Co., Ltd., Tokyo). Complete removal of the corneal endothelium from the Descemet's membrane was confirmed by staining the Descemet's membrane with 0.1% Trypan Blue stain.

Cultured RCECs were washed with PBS and trypsinized with 0.05% Trypsin-EDTA (Life Technologies) for five minutes at 37° C., and then neutralized with a culture medium. RCECs were washed three times and were preserved in a form of cell suspension at a cell density of $1.0 \times 10^6$ cells/300 µl of CTV in a 24-well plate (Ultra-Low Attachment). After preservation for 24, 48, or 72 hours, RCECs ($1.0 \times 10^6$ cells/300 µl of CTV) were gently mixed with a ROCK inhibitor (200 µM Y-27632 (Wako Pure Chemical Industries, Ltd.)/300 µl of CTV) to prepare RCECs for injection to rabbit eyes ($1.0 \times 10^6$ cells/600 µl of CTV, 100 µM Y-27632). A total of $5.0 \times 10^5$ RCECs with 300 µl of CTV including 100 µM Y-27632 was injected into the anterior chamber of the corneal endothelial decompensation model by using 26G needle. Rabbits were kept under general anesthesia while maintaining the endothelial surface in the bottom position for 3 hours. As a control, CTV including Y-27632 (final concentration: 100 µM) was injected into the anterior chamber of the corneal endothelial decompensation model. Eyes from three rabbits were used for each group (control, 24 hours, 48 hours, and 72 hours of cell preservation).

The anterior segment of the eyes were evaluated by slit-lamp microscopy for 14 days. Scheimpflug images were obtained by Pentacam® (OCULUS Optikgeräte GmbH, Wetzlar, Germany). The volume of 7 mm diameter of the cornea was also determined using Scheimpflug images. Central corneal thickness was measured with an ultrasound pachymeter (SP-2000; Tomey, Nagoya). Since the corneal thickness could not be measured due to severe edema, the thickness was regarded as 1200 µm, which is the instrument's maximum reading.

(Immunofluorescence and Actin Staining)

Rabbit corneas were retrieved and fixed in 4% formaldehyde for 10 minutes at room temperature. Samples were incubated with 1% bovine serum albumin at 37° C. for 45 minutes, and incubated overnight at 4° C. with antibodies against $Na^+/K^+$-ATPase (1:300, Upstate Biotechnology, Lake Placid, N.Y.), ZO-1 (1:300, Life Technologies Corp., Carlsbad, Calif.), and N-cadherin (1:300, BD Biosciences, San Jose, Calif.). After washing samples with PBS three times, the samples were incubated with Alexa Fluor® 488-conjugated goat anti-mouse (1:1000, Life Technologies) for 60 minutes at room temperature. Actin staining was performed on the incubated samples with Alexa Fluor® 488-conjugated phalloidin (1:400, Life Technologies) for 60 minutes at room temperature. Cell nuclei were stained with DAPI (Dojindo Laboratories, Kumamoto). The samples were examined with a fluorescence microscope (TCS SP2 AOBS; Leica Microsystems, Wetzlar, Germany).

(Statistical Analysis)

The statistical significance (P-value) for comparisons of multiple sample sets was determined with the Kruskal-Wallis test. Results are expressed as mean±standard deviation. A P value less than 0.05 was considered statistically significant.

(Results)
(Feasibility of Preserved RCECs for Cell Therapy in Rabbit Model)

Figure 3:
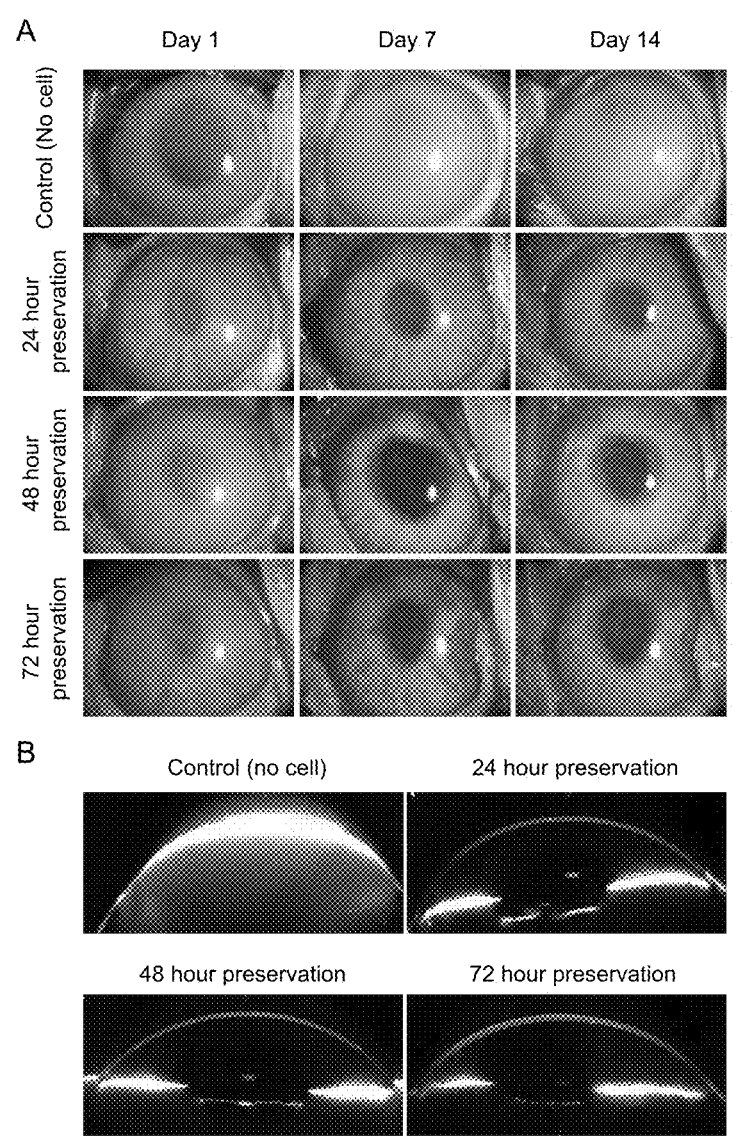
FIG. 3A shows slit lamp images of a rabbit model with injection of corneal endothelial cells preserved in a 24-well plate (Ultra-Low Attachment) into the anterior chamber.
FIG. 3B shows Scheimpflug images from day 14 after injection.

Cultured RCECs were harvested and preserved in a form of cell suspension in a 24 well plate (Ultra-Low Attachment) for 24, 48, or 72 hours at 37° C. Y-27632 was added to the RCECs before injection into a rabbit model, and they were injected into the anterior chamber of the rabbit corneal endothelial decompensation model. Slit lamp microscopy showed that the all eyes injected with RCECs after preservation for 24, 48, or 72 hours exhibited transparent cornea within 7 days (FIG. 3A). All control eyes exhibited hazy cornea due to corneal endothelial decompensation. While Scheimpflug images showed the successful regeneration of an anatomically normal cornea by injection of RCECs preserved for 24, 48, and 72 hours, the control eyes manifested severe corneal edema (FIG. 3B).

Figure 4:
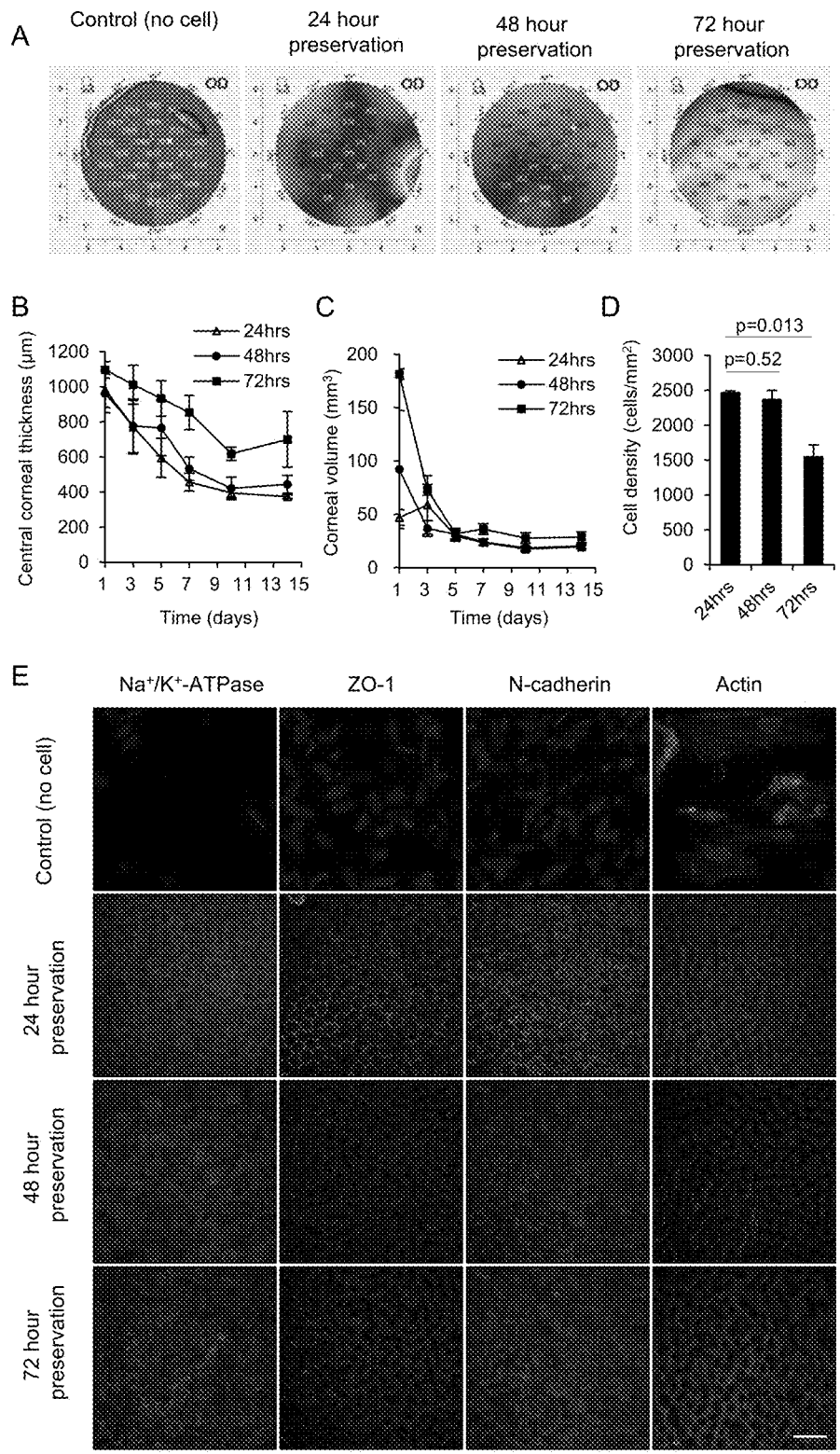
FIG. 4A shows a color map of the corneal thickness obtained with Pentacam™ on day 14 after injection in a rabbit model with injection of corneal endothelial cells preserved in a 24-well plate (Ultra-Low Attachment) into the anterior chamber.
FIG. 4B shows a graph of the central corneal thickness after injection of preserved corneal endothelial cells.
FIG. 4C shows a graph of the corneal volume after injection of preserved corneal endothelial cells.
FIG. 4D shows a graph of cell density in the eye on day 14 after injection of preserved corneal endothelial cells.
FIG. 4E shows a fluorescence microscope image of an immunofluorescently stained rabbit cornea. Blue indicates DAPI stain (cell nucleus). Green indicates, from the left, $Na^+/K^+$-ATPase, ZO-1, and N-cadherin.

A color map of corneal thickness obtained with Pentacam™ showed that RCECs preserved for 24 and 48 hours regenerated normal corneal thickness from the center to the periphery of the cornea after 14 days of RCEC injection. On the other hand, eyes injected RCECs preserved for 72 hours had thicker cornea, although the cornea was transparent upon observation using slit lamp microscopy (FIGS. 3A and 4A). An ultrasound pachymeter showed that the central corneal thickness reached approximately 400 µm (normal range) after 10 days in the eyes injected with RCECs preserved for 24 and 48 hours. However, the central corneal thickness of eyes injected with RCECs preserved for 72 hours decreased less than that of eyes injected with RCECs preserved for 24 and 48 hours and was significantly higher throughout 14 days (p<0.01) (FIG. 4B). Consistent with the central corneal thickness, the corneal volume determined by Scheimpflug images was lower in the eyes injected with RCECs preserved for 24 and 48 hours than in the eyes injected with RCECs preserved for 72 hours (FIG. 4C). The cell density of regenerated corneal endothelium evaluated by actin and DAPI was 2465 cells/mm$^2$ in the eyes injected with RCECs preserved for 24 hours and 2368 cells/mm$^2$ in the eyes injected with RCECs preserved for 48 hours. However, the cell density of eyes injected with RCECs preserved for 72 hours was 1548 cells/mm$^2$, which was a significant lower number than that of eyes injected with RCECs preserved for 24 or 48 hours (p<0.05) (FIG. 4D).

Immunofluorescent staining demonstrated that the function-related markers Na$^+$/K$^+$-ATPase (marker of pump function), ZO-1 (marker of tight junction), and N-cadherin (maker of adherence junction) were expressed in the lateral membrane of all regenerated CECs in eyes injected with RCECs preserved for 24, 48, and 72 hours. Actin staining showed that regenerated corneal endothelium forms a polygonal monolayer sheet like structure. On the other hand, only few cells, which expressed no function-related markers with fibroblastic change, were observed in control eyes due to corneal endothelial decompensation (FIG. 4E).

Example 3: Preservation of Corneal Endothelial Cells Using 1 ml Syringe (Materials and Methods)

HCECs were preserved at a cell density of 1.0×10$^6$ cells/300 μl in a form of a cell suspension in CTV for 72 hours in a 1 ml syringe (disposable syringe, filing no. 08B2X10007000001, Misawa Medical Industry Co., Ltd., Ibaraki). The syringe was laid down sideways and preserved at 37° C. for 72 hours. After preservation, the syringe was shaken with the fingertip. After the cells were moved out of the syringe with a 26G needle, the cell survival rate was evaluated. To evaluate the presence/absence of adhesion of cells being preserved to the inside surface of the syringe, the syringe was shaken with the fingertip after preservation, and the cells were removed from the syringe, and then the condition of the inside surface of the syringe after gently washing the inside surface of the syringe with a cell preservation medium was observed.

(Calculation of Bottom Area)

In each test, the amount of liquid was set at a constant amount of 300 μl. The bottom area was adjusted by adjusting the position of a piston. The inner diameter of the 1 ml syringe that was used was 6 mm. If the syringe is laid down sideways with the tip of the piston (rubber portion) located at a position that is 10 mm from the tip of the syringe, the bottom area would be (6×3.14/2)×10=94.2 mm$^2$=0.942 cm$^2$ according to the definition herein. The amount of air at this time is about 0 μl.

If the syringe is laid down sideways with the tip of the piston (rubber portion) located at a position that is 20 mm from the tip of the syringe, the bottom area would be (6×3.14/2)×20=188.4 mm$^2$=1.884 cm$^2$ according to the definition herein. The amount of air at this time is about 300 μl.

If the syringe is laid vertically with the tip of the piston (rubber portion) located at a position that is 20 mm from the tip of the syringe, the bottom area would be (6×6×3.14)≈28 mm$^2$=0.28 cm$^2$.

(Results)

Figure 5:
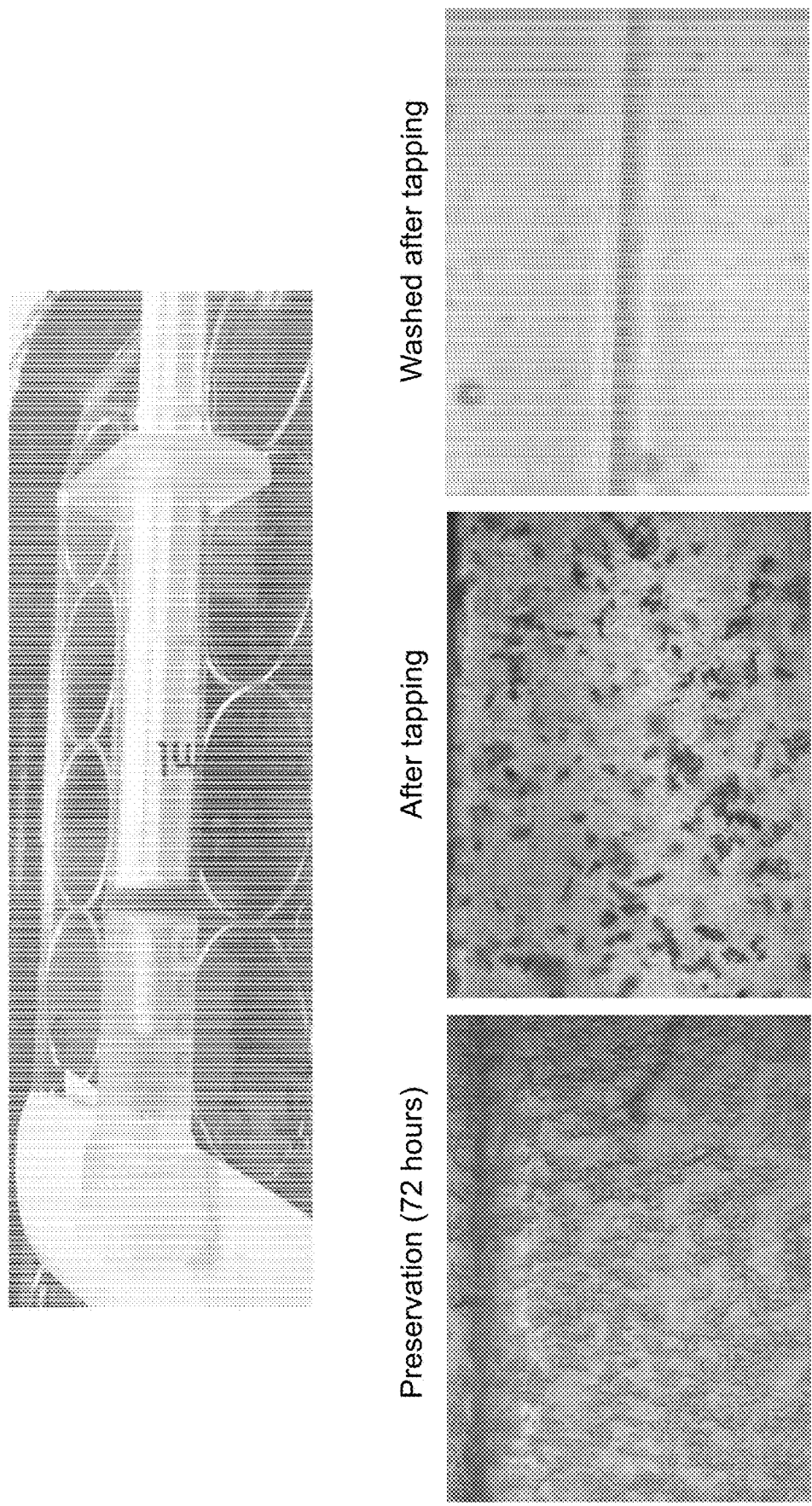
FIG. 5 shows 500 thousand cultured corneal endothelial cells that are suspended in 300 μl of cell preservation medium and preserved in a 1 ml syringe.

500 thousand cultured corneal endothelial cells were suspended in 300 μl of cell preservation medium and preserved in a 1 ml syringe (FIG. 5). After 72 hours of preservation of the corneal endothelial cells in the syringe, a deposition of cells on the side surface of the syringe was observed (FIG. 5, bottom left). After light tapping, the cells floated upwards from the side surface of the syringe, showing that the cells are not adhering to the inner surface of the syringe during preservation (FIG. 5, middle of bottom row). When the syringe was lightly tapped after 72 hours of preservation and the syringe was gently washed with a cell preservation medium, adhesion of cells to the side surface of the syringe was not observed (FIG. 5, bottom right).

Figure 6:
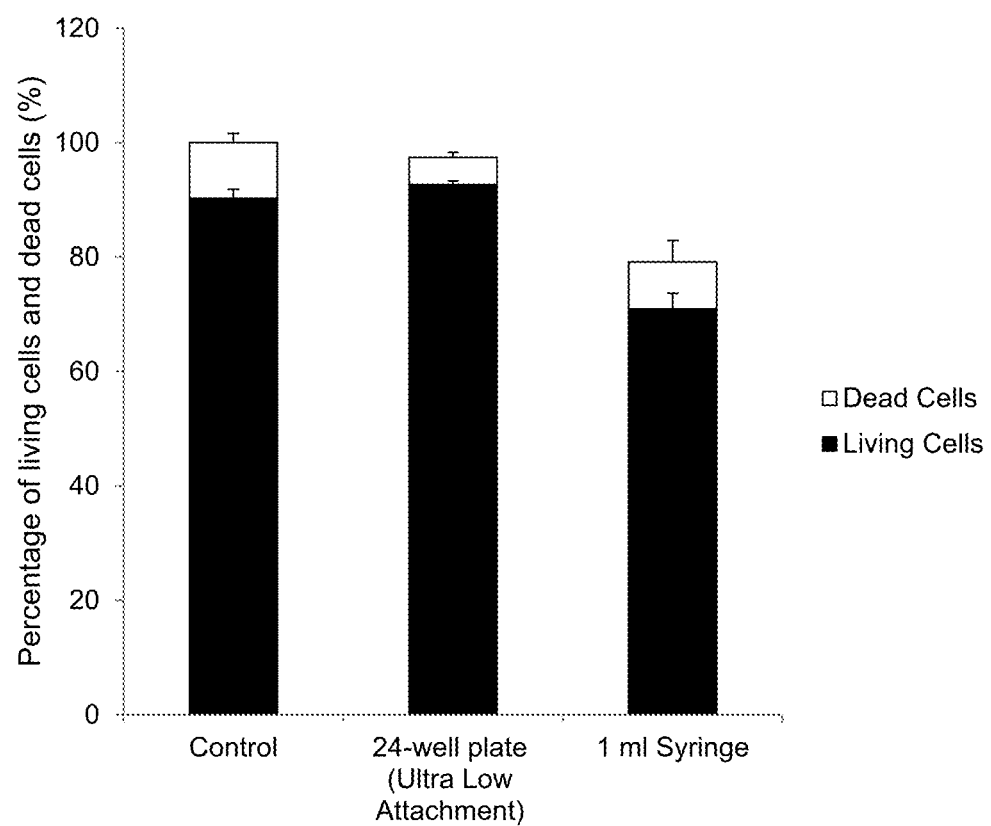
FIG. 6 shows a phase contrast microscope picture of corneal endothelial cells after 72 hours of preservation in a 1 ml syringe. The cells are deposited on the side surface of the syringe.
Figure 7:
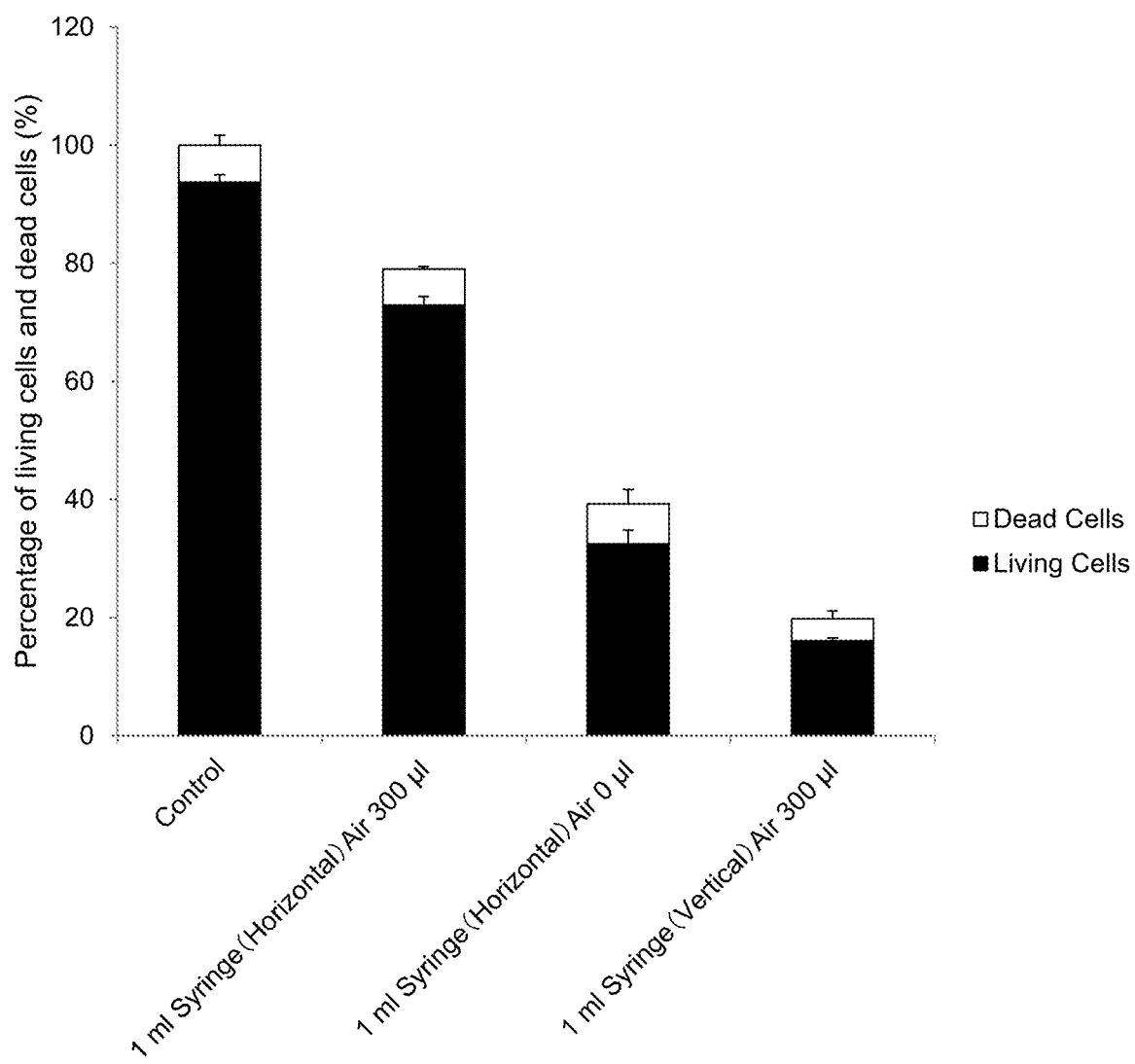
FIG. 7 shows a phase contrast microscope picture of corneal endothelial cells after 72 hours of preservation in a 1 ml syringe and light tapping. The cells have floated upwards from the side surface of the syringe.
Figure 8:
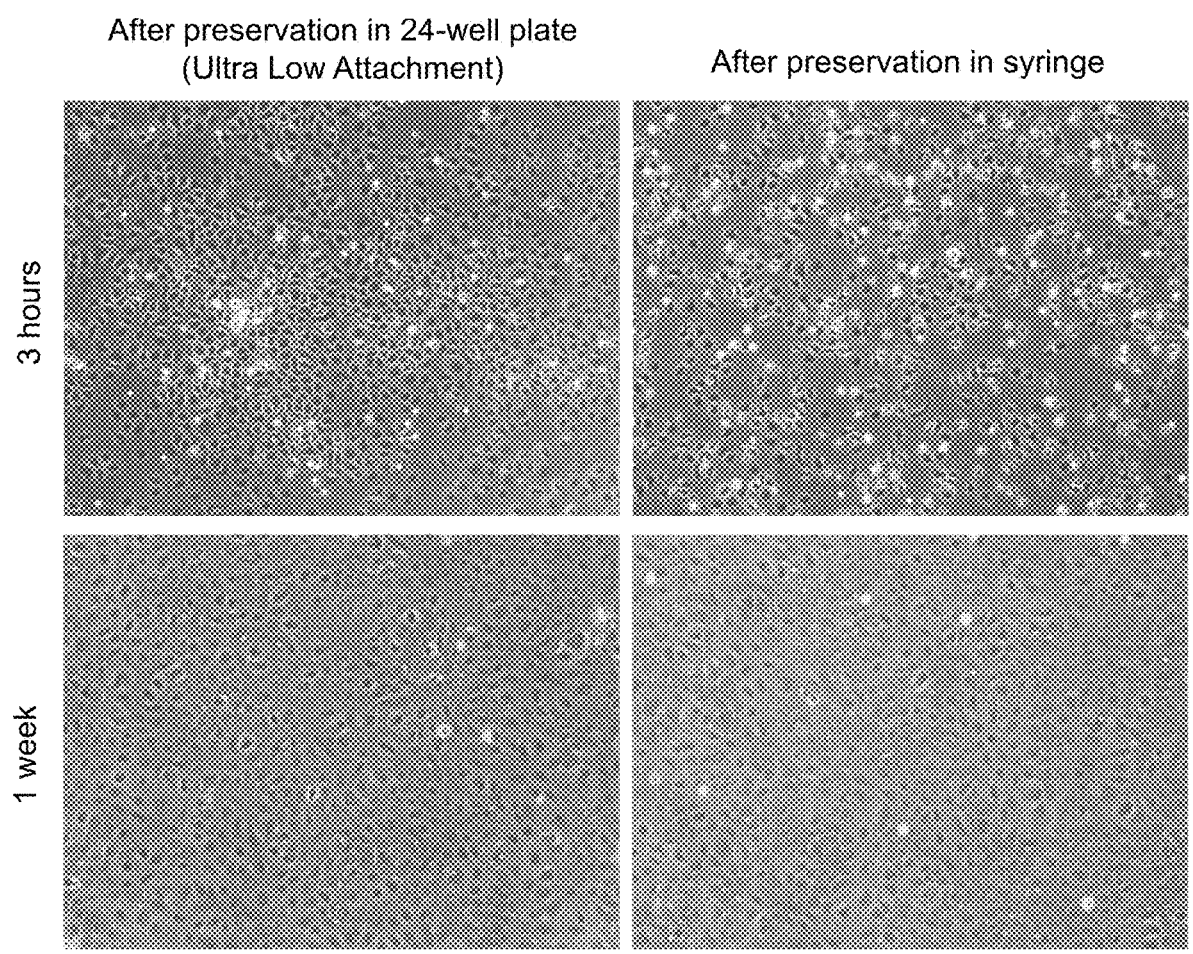
FIG. 8 shows a phase contrast microscope picture of corneal endothelial cells after 72 hours of preservation in a 1 ml syringe, light tapping, and gentle washing of the syringe with cell preservation medium. Adhesion of cells to the side surface of the syringe is not found.

Assuming all cells at the time of starting preservation to be 100%, the viable cell rate after 72 hours of preservation in the syringe was: 70.9% and dead cell rate: 8.2% with respect to (viable cell rate: 90.3% and dead cell rate: 9.7%), so that about 90% of cells survived, which was equivalent to the rate at the time of starting the preservation (FIG. 6). Meanwhile, the retrieved cell count was high when air was added and the syringe was laid on the side so that the bottom area inside the syringe was about 2 cm$^2$ upon preservation of cells in the syringe, but the retrieved cell count decreased to about half when air was not added so that the bottom area inside the syringe was about 1 cm$^2$. Similarly, the bottom area would be about 0.28 cm$^2$ if the syringe was held vertically with air inside the syringe, but the retrieved cell count significantly decreased (FIG. 7). This demonstrated that a bottom area of about 2 cm$^2$ increased the cell retrieval rate and survival rate upon cell preservation in a syringe.

Example 4: Detailed Study of Optimal Temperature Upon Cell Preservation (Materials and Methods)

(Culture of Corneal Endothelial Cells)

Five human donor corneas were obtained from diseased donors who were 40 years old or older. All corneas were preserved in Optisol (Chiron Vision, Irvine, Calif.) at 4° C. for 14 days or less before use. Human corneal endothelial cells (HCECs) were cultured in accordance with the following protocol. Briefly, Descemet's membranes containing corneal endothelia were mechanically peeled off from the donor corneas and digested by incubating with 1 mg/mL collagenase A (Roche Applied Science, Penzberg, Germany) at 37° C. for hours. After washing the HCECs with OptiMEM-I (Life Technologies Corp., Carlsbad, Calif.), the cells were seeded in one well of a 48-well plate coated with laminin E8 fragments (iMatrix-511; Nippi, Incorporated, Tokyo).

The medium was prepared according to the following protocol. Briefly, OptiMEM-I supplemented with 8% fetal bovine serum (FBS), 5 ng/mL epidermal growth factor (EGF; Thermo Fisher Scientific), 20 μg/mL ascorbic acid (Sigma-Aldrich, St. Louis, Mo.), 200 mg/L calcium chloride, 0.08% chondroitin sulfate (Sigma-Aldrich), and 50 μg/mL gentamicin (Thermo Fisher Scientific) were conditioned with NIH-3T3 for 24 hours. The conditioned medium was then collected, filtered through a 0.22 μm filtration unit (EMD Millipore Corporation, Billerica, Mass.), and used as a medium for HCECs.

The HCECs were cultured at 37° C. in humidified atmosphere containing 5% $CO_2$, and the medium was changed three times a week. For passaging the HCECs, cells were trypsinized with TrypLE™ Select Enzyme (10×) (Thermo Fisher Scientific) for five minutes at 37° C. and seeded at a 1:2 ratio. Cultured HCECs at passages 5 through 9 were used for this study.

The HCECs were washed with $Ca^{2+}$- and $Mg^{2+}$-free phosphate buffered saline (PBS) and trypsinized with TrypLE™ Select Enzyme (10×) for 15 minutes at 37° C. Cells were then recovered from the culture plate, washed twice, centrifuged at 280 G for three minutes, and suspended in OptiMEM-I. HCECs were preserved in a form of cell suspension at a cell density of $1.0 \times 10^6$ cells/300 µl in the aforementioned serum free vehicle (Cell Therapy Vehicle provided by Cell Science & Technology Institute, Inc. (Miyagi)) for 72 hours in a 24-well plate (Untreated) (AGC Techno Glass Co., Ltd., Shizuoka). To find the optimal temperature for HCEC preservation, HCECs were preserved under 9 temperature conditions, i.e., 12° C., 17° C., 22° C., 27° C., 32° C., 35° C., 37° C., 39° C., and 42° C.

After 72 hours of preservation, HCECs were recovered from cell culture plates with gentle pipetting, centrifuged at 280 G for three minutes, and resuspended in Cell Therapy Vehicle at a cell density of $1.0 \times 10^6$ cells/600 µl. Cell viability was determined by staining the dead cells with 0.5%-Trypan Blue stain (Nacalai tesque, Kyoto). As a control, HCECs recovered by trypsinization with TrypLE™ Select Enzyme (10×) were centrifuged at 280 G for three minutes, and resuspended in Cell Therapy Vehicle. Then, the cell survival rate was immediately evaluated without preservation in a form of a cell suspension.

(Results)

(Effect of the Temperature Condition in a Form of Cell Suspension on Cell Survival Rate)

Figure 9:
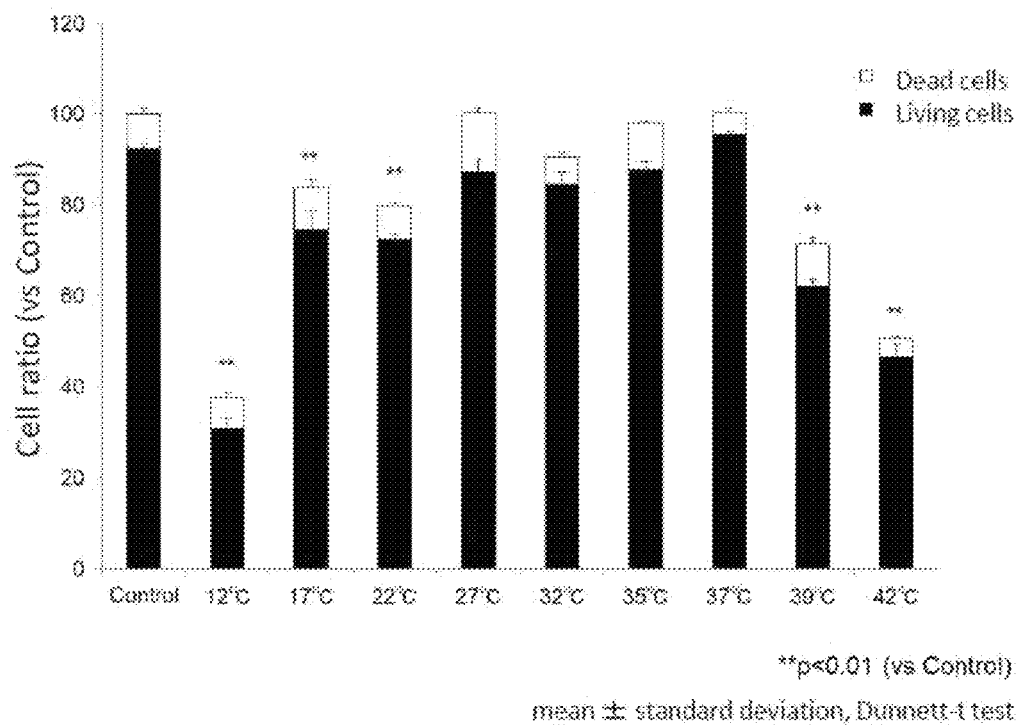
FIG. 9 shows the percentage of viable and dead corneal endothelial cells preserved at 12° C., 17° C., 22° C., 27° C., 32° C., 35° C., 37° C., 39° C., and 42° C. The white portion of a bar indicates dead cells, and the black portion indicates viable cells.

HCECs were preserved at a cell density of $1.0 \times 10^6$ cells/300 µl in a form of a cell suspension in CTV for 72 hours. Cells were retrieved with gentle pipetting, and the cell survival rate was evaluated (FIG. 9).

The viable cell rate is the highest in preservation at 37° C. among the 9 temperature conditions. Assuming all cells at the time of starting preservation to be 100%, the viable cell rate after 72 hours of preservation was: 95.4% and dead cell rate: 4.9% (with respect to the viable cell rate: 92.4% and dead cell rate: 7.6%), thus exhibiting similar cell survival rate to the rate at the time of starting the preservation. Under temperature conditions lower than 37° C., the viable cell rate decreased proportionally to the decrease in temperature. Preservation at 12° C., 17° C., and 22° C. exhibited a significantly lower viable cell rate compared to the viable cell rate at the time of stating the preservation, but a survival rate of 30% or greater was maintained. Under conditions of 39° C. and 42° C., the viable cell rate decreased proportionally to the increase in temperature and exhibited a significantly lower viable cell rate compared to the viable cell rate at the time of starting preservation, but a survival rate of 30% or greater was maintained. In this manner, preservation in the range of 12° C. to 42° C. where a survival rate of 30% or greater can be maintained is preferred, preservation in the range of 17° C. to 39° C. where a survival rate of 60% or greater can be maintained is more preferred, preservation in the range of 27° C. to 37° C. where a survival rate of 80% or greater can be maintained is still more preferred, and preservation at 37° C. where a survival rate of 90% or greater which is equivalent to a control can be maintained is most preferred.

Example 5: Study on Cell Preservation Using Glass Vial Bottle (Materials and Methods)

Figure 10:
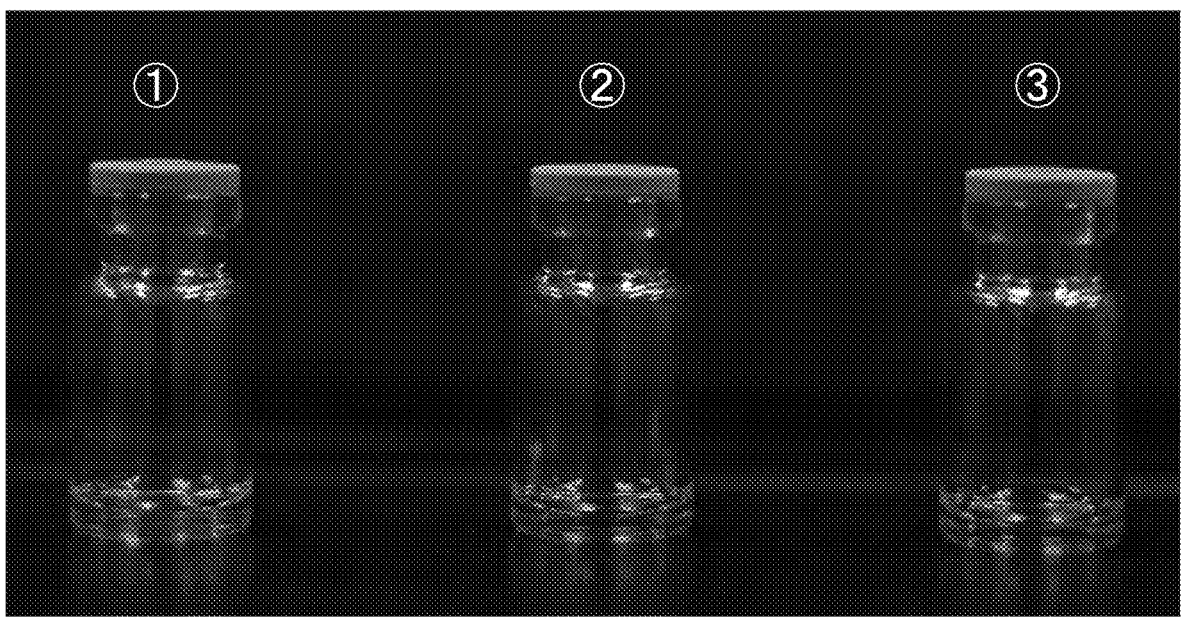
FIG. 10 shows a picture of (1) a vial bottle (Maruemu Corporation, Osaka, 0501-02), (2) a vial bottle (2 ml, diameter 16 mm, height 33 mm, IRAS treated, Iwata Glass Industrial Co., Ltd., Osaka, lot: 181024), and (3) a vial bottle (2 ml, diameter 16 mm, height 33 mm, IRAS treated and silica coating ($SiO_2$ coating), Iwata Glass Industrial Co., Ltd., Osaka, lot: 181102).

HCECs were preserved at a cell density of $1.0 \times 10^6$ cells/300 µl in a form of a cell suspension in CTV for 72 hours in a glass vial bottle. The following three glass vial bottles were used: vial bottle with a normal glass surface (Maruemu Corporation, Osaka, 0501-02); vial bottle subjected to low adhesion treatment (IRAS treatment) (Iwata Glass Industrial Co., Ltd., Osaka, lot: 181024); and vial bottle surface treated with silica (IRAS treated and $SiO_2$ coating) (Iwata Glass Industrial Co., Ltd., Osaka, lot: 181102) (FIG. 10). The bottom area of these vial bottles was about 2 cm².

After 72 hours of preservation, cells were recovered from vial bottles with gentle pipetting, centrifuged at 280 G for three minutes, and resuspended in Cell Therapy Vehicle at a cell density of $1.0 \times 10^6$ cells/600 µl. The cell survival rate was determined by staining the dead cells with 0.5% Trypan Blue stain (Nacalai tesque, Kyoto). As a control, HCECs recovered by trypsinization with TrypLE™ Select Enzyme (10×) were centrifuged at 280 G for three minutes, and resuspended in Cell Therapy Vehicle. Then, the cell survival rate was immediately evaluated without preservation in a cell suspension form.

(Results)

Figure 11:
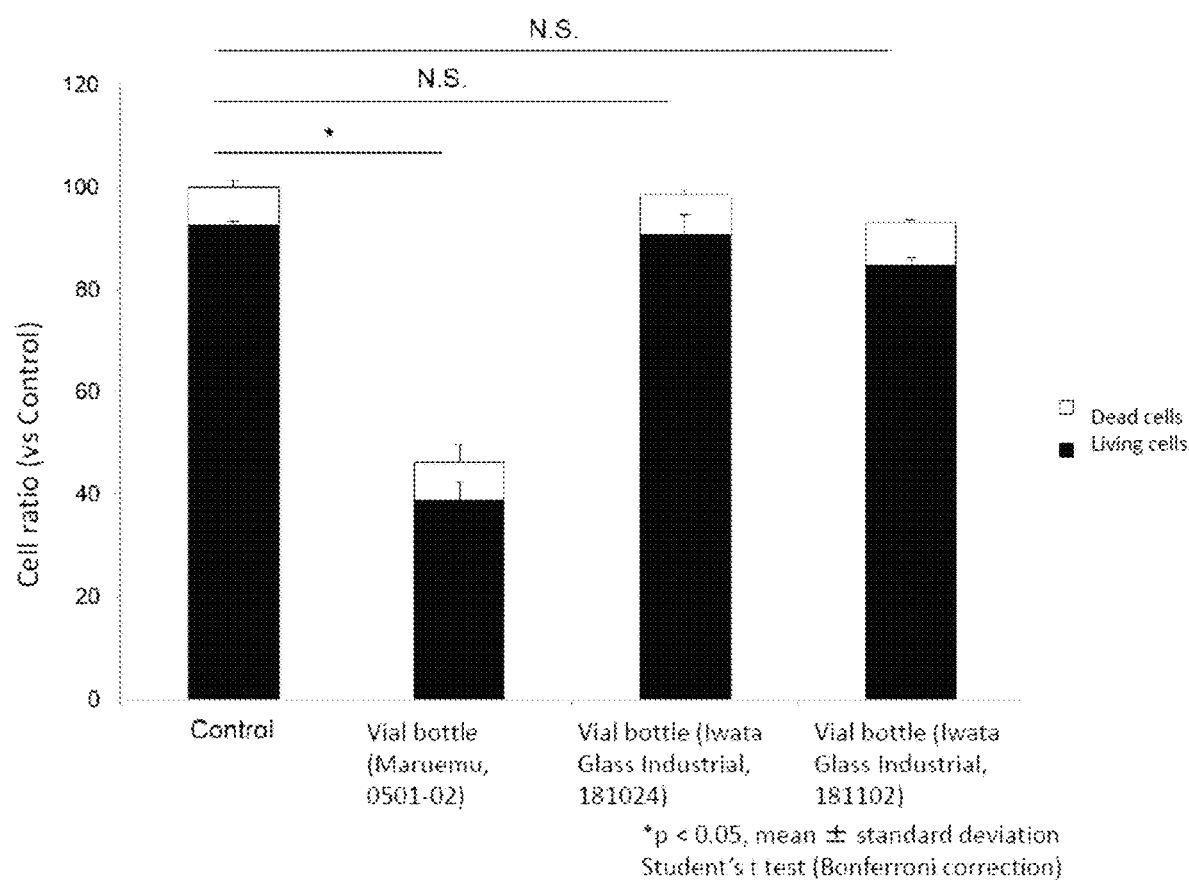
FIG. 11 shows the percentage of viable and dead corneal endothelial cells preserved in (1) a vial bottle (Maruemu Corporation, Osaka, 0501-02), (2) a vial bottle (2 ml, diameter 16 mm, height 33 mm, IRAS treated, Iwata Glass Industrial Co., Ltd., Osaka), and (3) a vial bottle (2 ml, diameter 16 mm, height 33 mm, IRAS treated and silica coating ($SiO_2$ coating), Iwata Glass Industrial Co., Ltd., Osaka). The white portion of a bar indicates dead cells, and the black portion indicates viable cells.

HCECs were preserved at a cell density of $1.0 \times 10^6$ cells/300 µl in a form of a cell suspension in CTV for 72 hours. Cells were retrieved with gentle pipetting, and the cell survival rate was evaluated (FIG. 11).

Cell adhesion to the vial bottle (Maruemu Corporation, Osaka, 0501-02) was observed. Meanwhile, there was no cell adhesion to the vial bottle (Iwata Glass Industrial Co., Ltd., Osaka, lot: 181024) and the vial bottle (Iwata Glass Industrial Co., Ltd., Osaka, lot: 181102) such that cells were able to be retrieved by gentle pipetting. Assuming all cells at the time of starting preservation to be 100%, the viable cell rate was 92.4% and dead cell rate was 7.6% for the control, whereas the viable cell rate was 38.9% and dead cell rate was 7.4% for cells preserved in the vial bottle (Maruemu Corporation, Osaka, 0501-02), thus exhibiting a significantly lower viable cell count compared to the viable cell count at the time of starting the preservation. The viable cell rate was 90.7% and dead cell rate was 7.8% for cells preserved in the vial bottle (Iwata Glass Industrial Co., Ltd., Osaka, lot: 181024), and the viable cell rate was 84.6% and dead cell rate was 8.4% for cells preserved in the vial bottle (Iwata Glass Industrial Co., Ltd., Osaka, lot: 181102), thus exhibiting a viable cell rate equivalent to the rate at the time of starting the preservation. In this manner, 30% cell survival rate was exhibited for all glass vial bottles, but the vial bottle with low adhesion surface treatment exhibited a higher cell survival rate.

Example 6: Manufacturing Example and Transport Example of Cell-Containing Product Corneal endothelial cells cultured from a donor cornea, corneal endothelial cells differentiated from iPS cells, ES cells, neural crest cells, or the like, or cells with the same function are collected from a culture dish by enzymatic treatment. The collected cells are suspended at a ratio of for example about 500 thousand to about 1 million cells to 300 µl of solution for cell injection. About 500 µl to about 800 µl of cell suspension is preserved in the vial bottle (Iwata Glass Industrial Co., Ltd., Osaka, lot: 181024) or the vial bottle (Iwata Glass Industrial Co., Ltd., Osaka, lot: 181102). The vial bottles are sealed with a rubber plug and aluminum (primary container). The vial bottles are further stored in a secondary container confirmed to have airtightness and leakage proof properties. The secondary container is preserved in an incubator maintained at 37° C. The secondary container is stored in an outer packaging container that absorbs external impact and transported to a medical institution in an environment maintained at 37° C.

As disclosed above, the present invention is exemplified by the use of its preferred embodiments. However, it is understood that the scope of the present invention should be interpreted based solely on the Claims. It is also understood that any patent, any patent application, and any references cited herein should be incorporated herein by reference in the same manner as the contents are specifically described herein. The present application claims priority to Japanese Patent Application No. 2018-187754 filed on Oct. 2, 2018 and Japanese Patent Application No. 2018-247970 filed on Dec. 28, 2018. The entire content thereof is incorporated herein by reference.

INDUSTRIAL APPLICABILITY

A method of preserving corneal endothelial cells is provided. Accordingly to the present invention, corneal endothelial cells can be preserved at a high cell survival rate. Corneal endothelial cells preserved in this manner have functions of normal corneal endothelial cells. Such cells can also be used as cells for treating a corneal endothelial disease or the like. Thus, the cells can be used in the pharmaceutical field and the like.

The invention claimed is:

1. A method of preserving corneal endothelial cells and/or corneal endothelium-like cells in a cell suspension state that can be used in cell injection therapy, comprising preserving the corneal endothelial cells and/or corneal endothelium-like cells in a container with a bottom area of at least about 0.7 $cm^2$, wherein a height of a liquid surface of a liquid for preserving the cells is about 0.75 mm or greater, and wherein the corneal endothelial cells and/or corneal endothelium-like cells are preserved for about 24 to 72 hours, wherein the preserved corneal endothelial cells and corneal endothelium-like cells are characterized by being administered without additional processing or culturing.

2. The method of claim 1, wherein the bottom area of the container is about 0.7 to about 4 $cm^2$.

3. The method of claim 1, wherein the bottom area of the container is about 1.5 to about 3 $cm^2$.

4. The method of claim 1, wherein the bottom area of the container is about 1.8 to about 2 $cm^2$.

5. The method of claim 1, wherein the container has not been surface treated for adherent culture.

6. The method of claim 1, wherein the container is a container with a low adhesion surface or a container with an untreated surface.

7. The method of claim 1, wherein the container is made of polystyrene, polypropylene, or glass.

8. The method of claim 1 wherein the container is selected from the group consisting of a 24-well plate, a vial bottle, a syringe, and a dish.

9. The method of claim 1, wherein the cells are preserved at a temperature of about 12° C. to about 42° C.

10. The method of claim 1, wherein the cells are preserved at a temperature of about 17° C. to about 39° C.

11. The method of claim 1, wherein the cells are preserved at a temperature of about 27° C. to about 37° C.

12. The method of claim 1, wherein the cells are preserved at a temperature of about 37° C.

13. The method of claim 1, wherein a cell density of the cells preserved in the container is about $1 \times 10^6$ cells/ml to about $8 \times 10^6$ cells/ml.

14. The method of claim 1, wherein a cell density of the cells preserved in the container is about $2 \times 10^6$ cells/ml to about $4 \times 10^6$ cells/ml.

15. The method of claim 1, wherein the container is sealed.

* * * * *